(12) United States Patent
Grushin et al.

(10) Patent No.: US 9,676,795 B2
(45) Date of Patent: Jun. 13, 2017

(54) PROCESS TO OBTAIN A TRIFLUOROMETHYLATING COMPOSITION

(75) Inventors: Vladimir Grushin, Tarragona (ES); Alessandro Zanardi, Tarragona (ES)

(73) Assignee: FUNDACIO INSTITUT CATALA D'INVESTIGACIO QUIMICA, Tarragona (ES)

( * ) Notice: Subject to any disclaimer, the term of this patent is extended or adjusted under 35 U.S.C. 154(b) by 625 days.

(21) Appl. No.: 14/000,116

(22) PCT Filed: Feb. 17, 2012

(86) PCT No.: PCT/EP2012/052759
§ 371 (c)(1),
(2), (4) Date: Jan. 21, 2014

(87) PCT Pub. No.: WO2012/113726
PCT Pub. Date: Aug. 30, 2012

(65) Prior Publication Data
US 2014/0235866 A1  Aug. 21, 2014

Related U.S. Application Data

(60) Provisional application No. 61/555,587, filed on Nov. 4, 2011.

(30) Foreign Application Priority Data

Feb. 25, 2011 (EP) .................................. 11382050

(51) Int. Cl.
| | | |
|---|---|---|
| C07F 1/08 | (2006.01) |
| C07B 39/00 | (2006.01) |
| C07C 17/32 | (2006.01) |
| C07C 201/12 | (2006.01) |
| C07F 1/00 | (2006.01) |
| C07C 41/30 | (2006.01) |
| C07C 45/45 | (2006.01) |
| C07C 45/68 | (2006.01) |

(52) U.S. Cl.
CPC ............... *C07F 1/08* (2013.01); *C07B 39/00* (2013.01); *C07C 17/32* (2013.01); *C07C 41/30* (2013.01); *C07C 45/455* (2013.01); *C07C 45/68* (2013.01); *C07C 201/12* (2013.01); *C07F 1/005* (2013.01)

(58) Field of Classification Search
CPC ....................................................... C07F 1/08
See application file for complete search history.

(56) References Cited

FOREIGN PATENT DOCUMENTS

| EP | 0320055 A2 * | 6/1989 | ............ C01G 3/006 |
| WO | 2012/024564 A1 | 2/2012 | |

OTHER PUBLICATIONS

Folleas et al. "Fluoroform: an Efficient Precursor for the Trifluoromethylation of Aldehydes" Tetrahedron, 2000, vol. 56, pp. 275-283.*
Wiemers et al. "Pregeneration, Spectroscopic Detection, and Chemical Reactivity of (Trifluoromethyl)copper, an Elusive and Complex Species" Journal of the American Chemical Society, 1986, vol. 108, pp. 832-834.*
Burton et al; "Fluorinated Organometallics: Perfluoroalkyl and Functionalized Perfluoroalkyl Organometallic Reagents in Organic Synthesis", Tetrahedron, vol. 48, No. 2, 1992, pp. 189-275.
Folleas et al; "Fluoroform: An Efficient Precursor for the Trifluormethylation of Aldeydes", Tetrahedron, vol. 56, 2000, pp. 275-283.
Purdy et al; "New Alkoxides of Copper and the Alkaline and Alkaline-Earth Metals", Inorganic Chemistry, American Chemical Society, Easton US, vol. 30, No. 13, 1991, pp. 2812-2819.

\* cited by examiner

*Primary Examiner* — Joseph Kosack
(74) *Attorney, Agent, or Firm* — Hayes Soloway PC

(57) ABSTRACT

Process to obtain a trifluoromethylating composition which comprises the reaction between a copper (I) source and a base in the presence of a solvent and between the resulting cuprating reagent with fluoroform.

11 Claims, No Drawings

PROCESS TO OBTAIN A TRIFLUOROMETHYLATING COMPOSITION

FIELD OF THE INVENTION

The present invention relates to a process to obtain a trifluoromethylating composition, to the trifluoromethylating composition obtainable by the process and to its use in trifluoromethylation reactions.

BACKGROUND OF THE INVENTION

Numerous organic compounds bearing a trifluoromethyl group are valuable as pharmaceuticals and agrochemicals. Examples of such pharmaceuticals bearing trifluoromethyl groups include Fluoxetine (Prozac®), Celecoxib (Celebrex®), Mefloquine (Lariam®), Leflunomide (Arava®), Nilutamide (Nilandron®), Dutasteride (Avodart®), Bicalutamide (Casodex®), Aprepitant (Emend). Examples of such agrochemicals include Trifluralin, Fipronil, Fluazinam, Penthiopyrad, Picoxystrobin, Fluridone and Norflurazon. Furthermore, some useful monomers, composites, materials for electronics, including electro- and photoluminescent compounds, solvents and valuable chemical building blocks and intermediates have the trifluoromethyl moiety. There is a need for simple, economic and environmentally benign methods to introduce the trifluoromethyl group into organic molecules in order to prepare active ingredients of agrochemicals and pharmaceuticals, as well as other useful compounds and materials.

A number of synthetic methods to produce such compounds have been developed. Particularly useful in this respect are copper reagents bearing the trifluoromethyl group. These trifluoromethyl copper reagents have been reviewed by Burton et al. ("Fluorinated organometallic compounds", Top. Curr. Chem. 1997, 193, 45 and Tetrahedron 1992, 48, 189), McClinton et al. ("Trifluoromethylations and related reactions in organic chemistry", Tetrahedron 1992, 48, 6555), Kumadaki ("Trifluoromethylation of Organic Compounds and Related Reactions", Synthesis 2010, 1865) and Schlosser ("CF$_3$-Bearing Aromatic and Heterocyclic Building Blocks", Angew. Chem. Int. Ed. 2006, 45, 5432). Various chemicals can be used to prepare such trifluoromethyl copper reagents, including CF$_3$I, CF$_3$Br, CF$_2$Br$_2$, CF$_2$BrCl, CF$_2$Cl$_2$, (CF$_3$)$_2$Hg, CF$_3$SiMe$_3$, CF$_3$CO$_2$X (X=Na, K, CH$_3$), FSO$_2$CF$_2$CO$_2$CH$_3$, as well as trifluoromethyl derivatives of Zn and Cd. Some of these compounds are toxic, some costly, some explosive and some environmentally malevolent, being ozone depleters.

Trifluoromethane (fluoroform or HFC-23), HCF$_3$, is readily available and inexpensive, has low toxicity and is not an ozone depleter. However, fluoroform has rarely been used to make trifluoromethyl copper compounds. For example, HCF$_3$ can be iodinated to CF$_3$I (Nagasaki "Study on a novel catalytic reaction and its mechanism for CF$_3$I synthesis." Catalysis Today 2004, 88, 121), which then can be contacted with copper metal to produce a trifluoromethyl, copper compound (McLoughlin and Thrower "Route to fluoroalkyl-substituted aromatic compounds involving fluoroalkylcopper intermediates." Tetrahedron 1969, 25, 5921). Alternatively, fluoroform can be deprotonated to produce the highly unstable CF$_3^-$ anion that easily decomposes into fluoride and difluorocarbene, prompt to form side products. For this reason, such reactions require low temperatures (below −20° C.), as well as the presence of N,N-dimethylformamide to stabilize the trifluoromethyl anion in the form of hemiaminolate, and are still hard to control. These compounds also suffer from lower reactivity than other trifluoromethyl copper compounds. However, no one has ever disclosed a direct synthesis of a trifluoromethyl copper compound directly from a copper reagent and fluoroform. Folleas et al. ("Fluoroform: an efficient precursor for the trifluoromethylation of aldehydes", Tetrahedron 2000, 56, 275) write: "Our first attempts to generate trifluoromethyl metal with M=Cu and Zn from fluoroform were based on the metallation concept with basic organocopper and organozinc derivatives in order to directly obtain the trifluoromethyl copper or zinc derivatives. However, whatever the organometallic used ((nBu)$_2$CuLi, (nBu)$_2$CuCNLi$_2$, (nBu)$_3$CuCNLi$_3$, tert-Bu$_2$CuCNLi$_2$, Et$_2$Zn, (nBu)$_3$ZnLi, Allyl-ZnBr, . . . ) in different conditions (heating, sonication, in pressurised flask) or different solvents (Et$_2$O, THF, HMPA) no trace of the corresponding trifluoromethyl organometallic was detected". Other basic Cu(I) compounds are known, for example dialkoxy copper(I) sodium derivatives (NaCu(OC(CH$_3$)$_3$)$_2$), polymers or oligomers thereof, and Na$_4$Cu$_4$(OC(C$_2$H$_5$)$_3$)$_8$. Some dialkoxy copper (I) lithium derivatives are also known: Li$_4$Cu$_4$(OC(CH$_3$)$_3$)$_8$ and LiCu(OCH$_3$)$_2$, as well as some dialkoxy copper (I) barium derivatives: Ba$_2$Cu$_4$(OC(C$_2$H$_5$)$_3$)$_8$, BaCu$_6$(OC(C$_2$H$_5$)$_3$)$_8$, BaCu$_2$(OC(CH$_3$)$_3$)$_4$ and polymers or oligomers thereof (Purdy "Structure and properties of heterometallic alkoxides containing copper (I)" Polyhedron 1995, 14, 761 and "Crystal structures of the Ba—Cu(I) alkoxides Ba$_4$Cu$_6$(O)(OCEt$_3$)$_{12}$ and BaCu$_6$(OCEt$_3$)$_8$" Polyhedron 1998, 17, 4041). However, no information is available regarding reactivity of these compounds toward fluoroform.

For the reasons stated above, it is needed to develop a method for obtaining a trifluoromethyl copper composition directly from a copper reagent and fluoroform, which is useful for synthetic transformations leading to the introduction of the trifluoromethyl group into other molecules in order to make useful materials.

DESCRIPTION OF THE INVENTION

The first aspect of the invention relates to a process to obtain a trifluoromethylating composition which comprises:

(i) contacting a copper (I) source and a base in the presence of a solvent; and (ii) reacting the cuprating reagent obtained in (i) and fluoroform.

The second aspect of the present invention relates to a trilfluoromethylating composition obtainable by the process defined above.

The third aspect of the present invention relates to the use of the trifluoromethylating composition defined above in the transfer of a trifluoromethyl group to an electrophile or to the carbon atom of an organoboron compound, preferably the electrophile is selected from aryl halides, heteroaryl halides, heterocyclyl halides, alkyl halides, alkynyl halides, alkenyl halides, allyl halides, acyl halides, aryl sulfonates, heteroaryl sulfonates, heterocyclyl sulfonates, alkyl sulfonates, alkenyl sulfonates, alkynyl sulfonates, allyl sulfonates, electron-deficient derivatives of Si, Ge, B, P, As, Sb, Bi, S, Se, Te and a metal atom in a metal compound, more preferably the electrophile is selected from aryl halides, heteroaryl halides, heterocyclyl halides, alkyl halides, alkynyl halides, alkenyl halides, allyl halides, acyl halides, aryl sulfonates, heteroaryl sulfonates, heterocyclyl sulfonates, alkyl sulfonates, alkynyl sulfonates, alkenyl sulfonates and allyl sulfonates, and even more preferably the electrophile is selected from aryl chlorides, aryl bromides, aryl iodides, heteroaryl chlorides, heteroaryl bromides and heteroaryl iodides.

The fourth aspect of the present invention relates to the use of the trifluoromethylating composition in the preparation of trifluoromethyl copper complexes.

The fifth aspect of the present invention relates to a cuprating reagent of formula I and polymers or oligomers thereof:

$$M_l S_m Cu_n (OR^1)_p X_q \qquad \mathrm{I}$$

wherein:
Cu is in the oxidation state of +1; and
M is lithium, sodium, potassium, rubidium, cesium, calcium, barium or magnesium; and
S is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2(1H)-pyrimidinone (DMPU), N-methylpyrrolidone (NMP), dimethylsulfoxide (DMSO), tetramethylurea (TMU), and hexamethylphosphoramide (HMPA);
$R^1$ is $C_1$-$C_{20}$ alkyl or $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
X is chloride, bromide or iodide;
l is an integer from 1 to 20;
m is an integer from 0 to 20;
n is an integer from 1 to 20;
p is an integer from 2 to 40;
q is an integer from 0 to 10; with the proviso that:
p is larger than n; and
the sum of l and n is equal to the sum of p and q when M is selected from lithium, sodium, potassium, rubidium and cesium; or
the sum of n and twice the value of l is equal to the sum of p and q when M is selected from calcium, magnesium and barium; and
with the proviso that the compound of formula I is not LiCu(OCH$_3$)$_2$, Li$_4$Cu$_4$(OC(CH$_3$)$_3$)$_8$, Ba$_2$Cu$_4$(OC(C$_2$H$_5$)$_3$)$_8$, BaCu$_6$(OC(C$_2$H$_5$)$_3$)$_8$, BaCu$_2$(OC(CH$_3$)$_3$)$_4$ or polymers or oligomers thereof, NaCu(OC(CH$_3$)$_3$)$_2$, Na$_4$Cu$_4$(OC(C$_2$H$_5$)$_3$)$_8$ or polymers or oligomers thereof.

The term "electrophile" is art-recognized and refers to a molecule bearing at least one electron-deficient atom that is prompt to accept one or more electrons from a reagent to allow for the formation of a new chemical bond. Electrophiles useful in the trifluoromethylation method of the present invention include olefins, alkynes, organic halides and sulfonates, electron-deficient derivatives of Si, Ge, B, P, As, Sb, Bi, S, Se, Te and metal atoms in some metal compounds. Examples of "electrophile" include, among others, aryl halides, heteroaryl halides, alkyl halides, alkynyl halides, alkenyl halides, allyl halides, acyl halides, heterocyclyl halides, aryl sulfonates, heteroaryl sulfonates, alkyl sulfonates, alkynyl sulfonates, heterocyclyl sulfonates, alkenyl sulfonates, allyl sulfonates, boron trichloride and phosphorus trichloride.

The term "halide" means fluoride, chloride, bromide or iodide.

The term "halo" means fluoro, chloro, bromo or iodo.

The term "aryl" is art-recognized and refers to 5-, 6-, and 7-membered single ring aromatic groups which can be optionally fused to one or more 3- to 20-membered carbocyclic or heterocyclic rings that can be saturated, unsaturated or aromatic. Aryl can thus be either monocyclic or polycyclic. Examples of aryl include, but are not limited to, phenyl, napthyl, anthracenyl, biphenylyl, and terphenylyl. Aryl may be optionally substituted with one or more substituents at any available position. Examples of these substituents include, among others, halo-, nitro-, cyano-, alkyl, cycloalkyl, hydroxyl, alkenyl, alkynyl, alkoxyl, aralkoxyl, aroxyl, amino, amido, carbonyl, carboxyl, sulfhydryl, alkylthio, sulfonyl, sulfonamido, imino, ketone, ether, ester, aldehyde, azido, perfluoroalkyl, amido, imino, heterocyclyl, aromatic and heteroaromatic groups.

The term "alkyl" is art-recognized and refers to aliphatic saturated groups including linear, cyclic or branched alkyl groups. Examples include, among others, methyl, ethyl, pentyl, heptyl, tert-butyl, iso-propyl and cyclohexyl. Carbon atoms in the alkyl may be substituted at one or more positions with substituents including, among others, halo-, nitro-, cyano-, alkyl, cycloalkyl, hydroxyl, alkenyl, alkynyl, alkoxyl, aralkyl, aralkoxyl, aroxyl, amino, amido, carbonyl, carboxyl, sulfhydryl, alkylthio, aryl, arylthio, sulfonyl, sulfonamido, imino, ketone, ether, ester, aldehyde, azido, perfluoroalkyl, amido, imino, heterocyclyl, aromatic and heteroaromatic groups.

The term "$C_1$-$C_{20}$ alkyl", as a group or part of a group, means a straight-chain, cylic or branched saturated aliphatic group which contains from 1 to 20 carbon atoms and which is optionally substituted at any available position with one or more $C_1$-$C_{20}$ alkoxy, $C_5$-$C_7$ aryl or $C_5$-$C_7$ aryloxy. Examples of "$C_1$-$C_{20}$ alkyl" include, among others, methyl, ethyl, neo-pentyl, hexyl, pentyl, heptyl, tert-butyl, iso-propyl and cyclohexyl.

The term "Et" is used to refer to the ethyl radical of formula —$C_2H_5$.

The terms "tert-Bu", "t-Bu", "Bu-t" and "tert-butyl" are interchangeable and are used to refer to the tert-butyl group of formula —$C(CH_3)_3$.

The term "$C_5$-$C_7$ aryl" as a group or part of a group, means a 5-, 6-, and 7-membered aryl as defined above, optionally fused to one or more 3 to 7-membered saturated, unsaturated or aromatic carbocyclic rings. $C_5$-$C_7$ aryl may optionally be substituted at any available position with one or more $C_1$-$C_{20}$ alkyl, $C_1$-$C_{20}$ alkoxy, $C_5$-$C_7$ aryl, or $C_5$-$C_7$ aryloxy. Examples include, among others, phenyl, naphthyl, biphenylyl and anthracenyl.

The term "sulfonate" is art-recognized and refers to a fragment that is represented by formula II:

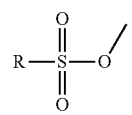

wherein:
R is $C_1$-$C_{20}$ alkyl, $C_5$-$C_7$ aryl or $C_yF_{2y+1}$; and
y is from 1 to 14.
Examples include, among others, methyl sulfonate, 4-tolylsulfonate, phenyl sulfonate, trifluoromethyl sulfonate, perfluorobutylsulfonate and 4-nitrophenylsulfonate.

The term "alkenyl" is art-recognized and refers to unsaturated aliphatic groups similar to alkyl as defined above, but containing one carbon-carbon double bond, optionally substituted at one or more positions with substituents selected from, but not limited to, halo-, nitro-, cyano-, alkyl, cycloalkyl, hydroxyl, alkenyl, aryl, arylthio, alkynyl, alkoxyl, aralkoxyl, aroxyl, amino, amido, carbonyl, carboxyl, sulfhydryl, alkylthio, sulfonyl, sulfonamido, imino, ketone; ether, ester, aldehyde, azido, perfluoroalkyl, amido, imino, heterocyclyl, aromatic and heteroaromatic groups.

The term "alkynyl" is art-recognized and refers to unsaturated aliphatic groups similar to alkyl as defined above, but containing one carbon-carbon triple bond, optionally substituted at one or more positions with substituents selected from, but not limited to, halo-, nitro-, cyano-, alkyl, cycloalkyl, hydroxyl, alkenyl, aryl, arylthio, alkynyl, alkoxyl, aralkyl, aralkoxyl, amino, amido, carbonyl, carboxyl, sulfhydryl, alkylthio, sulfonyl, sulfonamido, imino, ketone, ether, ester, aldehyde, azido, perfluoroalkyl, amido, imino, heterocyclyl, aromatic and heteroaromatic groups.

The term "allyl" is art-recognized and refers to a substituent derived from alkenyl with the connection site being separated from the double bond by one C—C bond. Allyl may be substituted at one or more positions with substituents selected from, but not limited to, halo-, nitro-, cyano-, alkyl, cycloalkyl, hydroxyl, alkenyl, aryl, arylthio, alkynyl, alkoxyl, aralkoxyl, aroxyl, amino, amido, carbonyl, carboxyl, sulfhydryl, alkylthio, sulfonyl, sulfonamido, imino, ketone, ether, ester, aldehyde, azido, perfluoroalkyl, amido, imino, heterocyclyl, aromatic and heteroaromatic groups.

The term "acyl" is art-recognized and refers to a group selected from alkyl, aryl, aralkyl, heteroaryl, heterocyclyl, alkenyl, alkynyl and allyl, substituted at any position with a C=O group and the carbon atom of this group being the connection site. Examples include, among others, acyl, butyryl, benzoyl, naphthoyl, palmoyl. Acyl may be substituted at one or more positions with substituents selected from, but not limited to, halo-, nitro-, cyano-, alkyl, cycloalkyl, hydroxyl, alkenyl, alkynyl, aryl, arylthio, alkoxyl, aralkoxyl, aroxyl, amino, amido, carbonyl, carboxyl, sulfhydryl, alkylthio, sulfonyl, sulfonamido, imino, ketone, ether, ester, aldehyde, azido, perfluoroalkyl, amido, imino, heterocyclyl, aromatic and heteroaromatic groups.

The term "heteroaryl" is art-recognized and refers to 5-, 6-, and 7-membered single ring aromatic groups whose rings include from one to four heteroatoms selected from N, O, and S, and which can be optionally fused to one or more 3- to 20-membered carbocyclic or heterocyclic rings that can be saturated, unsaturated or aromatic. Heteroaryl can thus be either monocyclic or polycyclic. Examples of "heteroaryl" include, among others, pyridine, quinoline, isoquinoline, pyrrole, thiophene, pyrimidine, indole and the like. The heteroaryl may be optionally substituted with one or more substituents at any available position. Examples of these substituents include, among others, halo-, nitro-, cyano-, alkyl, cycloalkyl, hydroxyl, alkenyl, aryl, arylthio, alkynyl, alkoxyl, aralkoxyl, aroxyl, amino, amido, carbonyl, carboxyl, sulfhydryl, alkylthio, sulfonyl, sulfonamido, imino, ketone, ether, ester, aldehyde, azido, perfluoroalkyl, amido, imino, heterocyclyl, aromatic and heteroaromatic groups.

The terms "heterocyclyl" or "heterocyclic group" are art-recognized and refer to 3 to 24-membered single ring groups, each member being independently selected from C, CH, $CH_2$, N, NH, O, S, CO, SO and $SO_2$, and optionally fused to one or more 3- to 20-membered carbocyclic or heterocyclic rings that can be saturated, unsaturated or aromatic. Heterocyclyl groups include, for example, pyrrolidine, tetrahydrofuran, tetrahydropyran, piperidine and dioxane. The heterocyclic rings may be substituted at one or more ring positions with substituents including, but not limited to, halo-, nitro-, cyano-, alkyl, cycloalkyl, hydroxyl, alkenyl, aryl, arylthio, alkynyl, alkoxyl, aralkoxyl, aroxyl, amino, amido, carbonyl, carboxyl, sulfhydryl, alkylthio, sulfonyl, sulfonamido, imino, ketone, ether, ester, aldehyde, azido, perfluoroalkyl, amido, imino, heterocyclyl, aromatic and heteroaromatic groups.

The term "metal" is art-recognized and means a substance with high conductivity of heat and electricity, luster and malleability, which readily loses electrons to form positive ions (cations). Examples include, among others, copper, zinc, cadmium, iron, nickel, palladium, cobalt, gold, silver, iridium, ruthenium, rhenium, rhodium, chromium, molybdenum, indium and manganese. Therefore, a "metal atom in a metal compound" refers to a metal atom that is part of a coordination compound of said metal with one or more ligands.

The term "$C_1$-$C_{20}$ alkoxy" as a group or part of a group, means a group of formula —$OC_1$-$C_{20}$ alkyl, wherein the $C_1$-$C_{20}$ alkyl moiety has the same meaning as previously described, and wherein $C_1$-$C_{20}$ alkoxy is optionally substituted at any available position with one or more $C_5$-$C_7$ aryl, $C_1$-$C_{20}$ alkoxy and $C_5$-$C_7$ aryloxy. Examples include, among others, methoxy, ethoxy, propoxy, isopropoxy, butoxy, isobutoxy, sec-butoxy, neo-pentoxy, benzyloxy and tert-butoxy.

The term "$C_5$-$C_7$ aryloxy" as a group or part of a group, means a group of formula —$OC_5$-$C_7$ aryl, wherein the $C_5$-$C_7$ aryl moiety has the same meaning as previously described and wherein $C_5$-$C_7$ aryloxy is optionally substituted at any available position with one or more $C_1$-$C_{20}$ alkoxy, $C_5$-$C_7$ aryl or $C_1$-$C_{20}$ alkyl. Examples include, among others, phenoxy and 1-naphthyloxy.

A "base" in chemistry is a substance that can accept protons or more generally, donate electron pairs. Examples of bases include, among others, sodium hydroxide, potassium hydroxide, calcium hydroxide, alkali metal alkoxides, alkali metal aryloxides, ammonia, pyridine, triethylamine and the like.

The term "ligand" is art-recognized and means an ion, atom, or molecule that binds to a metal. Ligands are usually bases with at least one lone electron pair available for coordination to the metal. The ligand may be monodentate, bidentate, or higher. Suitable ligands include organic compounds containing heteroatoms such as nitrogen, phosphorus, oxygen and sulfur. Examples of such compounds include, but are not limited to, 1,10-phenanthroline and its derivatives, 2,2'-bipyridyl and its derivatives, pyridine and its derivatives, mono-, di- and polydentate phosphines, carbenes, as well as mixed ligands containing two or more different heteroatoms.

The term "cupration" means a one-step process of direct displacement of a hydrogen atom on a molecule by a copper atom. Therefore, a cuprating reagent is a reagent able to displace in a one-step process a hydrogen atom on a molecule by a copper atom, optionally bearing one or more ligands.

The term "gram-mole" is art-recognized and means the amount of a substance that contains as many molecules as there are atoms in 12 g of the isotope carbon-12 ($^{12}C$).

The term "gram-atom" is art-recognized and means the amount of an element that contains as many of its atoms as there are atoms in 12 g of the isotope carbon-12 ($^{12}C$).

The term "catalyst" means a substance that increases the rate of a chemical reaction while being used in a molar quantity that is smaller than the molar quantity of the reactants and reagents. For example, platinum metal is a catalyst for the reaction of hydrogen and oxygen to produce water. In another example, palladium is a catalyst for the hydrogenation of olefins. In another example, phosphoric acid is a catalyst for the addition of water to ethylene to give ethanol.

The term "copper (I) source" means a substance or mixtures of substances containing a copper (I) compound available for a desired transformation involving copper (I). Examples include, among others, copper (I) chloride, copper (I) bromide, copper (I) iodide, copper (I) cyanide, copper (I) oxide, copper (I) trifluoromethanesulfonate, tetrakis(acetonitrile)copper (I) tetrafluoroborate, tetrakis(acetonitrile) copper (I) tetraphenylborate, tetrakis(acetonitrile)copper (I) hexafluorophosphate, tetrakis(acetonitrile)copper (I) trifluoromethanesulfonate, copper (I) sulfide, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, [Cu(PPh$_3$)$_3$]Br, [Cu(PPh$_3$)$_3$]F, [Cu(PPh$_3$)$_3$]Cl, Cu(OCOR$^2$), Cu(SR$^2$), Cu(SR$^2_2$)Br, Cu(SR$^2_2$)Cl, Cu(SR$^2_2$)I, Cu(OSO$_2$R$^2$), CuOR$^2$, wherein R$^2$ is selected from alkyl, preferably C$_1$-C$_{20}$ alkyl, optionally substituted with one or more aryl, alkoxy and aryloxy and from aryl, preferably C$_5$-C$_7$ aryl, optionally substituted with one or more alkyl, aryl, alkoxy and aryloxy and mixtures thereof. In addition, "copper (I) source" means a substance or mixtures of substances containing copper in any other oxidation state, provided it can be converted to copper in the oxidation state of +1 by means of reduction or oxidation, either chemically or electrochemically.

The term "copper available to form the cuprating reagent" refers to the amount of copper atoms present in the reaction mixture that can bind to the oxygen atoms of more than one anion selected from the anions of formula $^-$OR$^1$, $^-$OR$^2$ and mixtures thereof, wherein R$^1$ and R$^2$ are as defined above. In the field of the invention, a ligand can be used to scavenge some copper (I) atoms. Depending on the denticity of the ligand and its amount used, a defined number of copper (I) atoms will be coordinated to that ligand, and thus made unavailable for the process of the invention. In this way, the ratio of copper (I) to the base can be adjusted and controlled to achieve the desired cuprating composition. The "copper available to form the cuprating reagent" refers to those copper (I) atoms that are not coordinated to the ligand and that present the ability to form the compounds of formula I in the presence of a base.

A process performed "sequentially" refers to a process involving two or more steps, in which a reactant or reagent obtained in one step is stored, either as a composition or as an isolated compound, prior to its use in the next step involving other reagents or reactants.

The expression "optionally substituted with one or more" means that a group can be substituted with one or more substituents. The substituents can be the same or different and can be placed in any available position.

The term "solid-liquid separation techniques" refers to the methods known in the state of the art to separate the solid suspended in, or precipitated from, a solution. Examples include, among others, filtration, centrifugation, and decantation.

The term "organoboron compound" refers to a chemical compound containing at least one boron-carbon covalent bond. Examples include, among others, boranes, boronates and boronic acids.

The term "trifluoromethylcopper compound" refers to a chemical compound containing a Cu—CF$_3$ bond. Examples include, among others, (1,10-phenanthroline) trifluoromethylcopper (I) of the formula [CuCF$_3$(1,10-phenanthroline)], (1,10-phenanthroline)(triphenylphosphine) trifluoromethylcopper (I) of the formula [CuCF$_3$(1,10-phenanthroline)(PPh$_3$)], tris(triphenylphosphine)trifluoromethyl copper (I) of the formula [CuCF$_3$(PPh$_3$)$_3$] and [CuCF$_3$[1,3-bis(2,6-diisopropylphenyl)imidazol-2-ylidene].

The term "atmospheric pressure" refers to the force per unit area applied to a surface by the weight of air above that surface in the atmosphere. Atmospheric pressure usually ranges from 0.9 bar to 1.1 bar, preferably the accepted value of atmospheric pressure is 1.013 bar.

A process "performed continuously" means a flow process that allows for a continuous production of the product by constant feeding of reactants and solvent in the right proportions.

The term "oxidant" refers to a chemical compound prompt to accept one or more electrons from another reagent within a RedOx chemical reaction. Examples include, among others, oxygen, perchlorate anions, oxone, percarboxylic acids and peroxides.

In another embodiment, the invention relates to a process to obtain a trifluoromethylating composition as defined above, wherein (i) and (ii) are performed by mixing together the copper (I) source, the base, the solvent and fluoroform.

In another embodiment, the invention relates to a process to obtain a trifluoromethylating composition as defined above wherein (i) and (ii) are performed by mixing together the copper (I) source, the base, the solvent, and fluoroform and stirring the reaction mixture.

In another embodiment, the invention relates to a process to obtain a trifluoromethylating composition as defined above, wherein (i) and (ii) are performed sequentially.

In another embodiment, the invention relates to a process to obtain a trifluoromethylating composition as defined above wherein (i) and (ii) are performed sequentially and the cuprating reagent obtained in (i) is stored prior to its use in (ii), preferably for from 0.5 minutes to 30 days.

In another embodiment, the invention relates to a process to obtain a trifluoromethylating composition as defined above wherein (i) and (ii) are performed sequentially and the cuprating reagent obtained in (i) is isolated and stored prior to its use in (ii); preferably the cuprating reagent obtained in (i) is isolated and stored protected from oxygen and moisture prior to its use in (ii).

In another embodiment, the invention relates to a process to obtain a trifluoromethylating composition as defined above, wherein the solvent is a polar aprotic solvent.

In another embodiment, the invention relates to a process to obtain a trifluoromethylating composition as defined above, wherein the solvent is selected from N,N-dimethylformamide (DMF), 1,3-dimethyl-2-imidazolidinone (DMI), N-dimethylacetamide (DMAC), 1,3-dimethyl-3,4,5,6-tetrahydro-2(1H)-pyrimidinone (DMPU), N-methylpyrrolidone (NMP), dimethylsulfoxide (DMSO), tetramethylurea (TMU), hexamethylphosphoramide (HMPA), and mixtures thereof.

In another embodiment, the invention relates to a process to obtain a trifluoromethylating composition as defined above, wherein the solvent is anhydrous.

In another embodiment, the invention relates to a process to obtain a trifluoromethylating composition as defined above, wherein the solvent is selected from anhydrous N,N-dimethylformamide (DMF), anhydrous 1,3-dimethyl-2-imidazolidinone (DMI), anhydrous N-dimethylacetamide (DMAC), anhydrous 1,3-dimethyl-3,4,5,6-tetrahydro-2(1H)-pyrimidinone (DMPU), anhydrous N-methylpyrrolidone (NMP), anhydrous dimethylsulfoxide (DMSO), anhydrous tetramethylurea (TMU), anhydrous hexamethylphosphoramide (HMPA), and mixtures thereof; preferably the solvent is selected from anhydrous N,N-dimethylformamide (DMF), anhydrous N-methylpyrrolidone (NMP) and mixtures thereof.

In another embodiment, the invention relates to a process to obtain a trifluoromethylating composition as defined above, wherein the copper (I) source is generated in situ from a copper (II) or a copper (III) compound and a reducing agent.

In another embodiment, the invention relates to a process to obtain a trifluoromethylating composition as defined above, wherein the copper (I) source is generated in situ from metallic copper and an oxidizing agent.

In another embodiment, the invention relates to a process to obtain a trifluoromethylating composition as defined above, wherein the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OR$^2$), Cu(OCOR$^2$), Cu(SR$^2$), Cu(SR$^2_2$)Br, Cu(SR$^2_2$)Cl, Cu(SR$^2_2$)I, Cu(OSO$_2$R$^2$) and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy.

In another embodiment, the invention relates to a process to obtain a trifluoromethylating composition as defined above, wherein the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2_2$)Br, Cu(SR$^2_2$)Cl, Cu(SR$^2_2$)I, Cu(OSO$_2$%$^2$) and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy.

In another embodiment, the invention relates to a process to obtain a trifluoromethylating composition as defined above, wherein the copper (I) source is selected from CuOR$^2$ and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy.

In another embodiment, the invention relates to a process to obtain a trifluoromethylating composition as defined above, wherein the copper (I) source is selected from copper (I) chloride, copper (I) bromide, copper iodide, copper (I) acetate, copper (I) trifluoromethanesulfonate, and mixtures thereof.

In another embodiment, the invention relates to a process to obtain a trifluoromethylating composition as defined above, wherein the copper (I) source is selected from copper (I) chloride, copper (I) bromide, copper iodide and mixtures thereof, preferably the copper (I) source is copper (I) chloride.

In another embodiment, the invention relates to a process to obtain a trifluoromethylating composition as defined above wherein the base is selected from alkali metal alkoxide, alkali metal aryloxide and mixtures thereof.

In another embodiment, the invention relates to a process to obtain a trifluoromethylating composition as defined above wherein the base is a compound of formula III or mixtures thereof, $$MOR^1 \quad\quad III$$

wherein:
M is selected from potassium, sodium, rubidium and cesium; and
R$^1$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy.

In another embodiment, the invention relates to a process to obtain a trifluoromethylating composition as defined above wherein the base is a compound of formula III or mixtures thereof wherein:
M is selected from potassium and sodium; and
R$^1$ is C$_1$-C$_{20}$ alkyl.

In another embodiment, the invention relates to a process to obtain a trifluoromethylating composition as defined above wherein the base is a compound of formula III or mixtures thereof wherein:
M is selected from potassium and sodium; and
R$^1$ is selected from the group consisting of methyl, ethyl, propyl, iso-propyl, butyl, iso-butyl, tert-butyl, pentyl and neo-pentyl.

In another embodiment, the invention relates to a process to obtain a trifluoromethylating composition as defined above wherein the base is selected from potassium tert-butoxide, sodium tert-butoxide, potassium methoxide and mixtures thereof.

In another embodiment, the invention relates to a process to obtain a trifluoromethylating composition as defined above wherein the base is selected from potassium tert-butoxide, sodium tert-butoxide and mixtures thereof.

In another embodiment, the invention relates to a process to obtain a trifluoromethylating composition as defined above wherein the base is selected from potassium tert-butoxide, potassium methoxide and mixtures thereof; preferably the base is potassium tert-butoxide.

In another embodiment, the invention relates to a process to obtain a trifluoromethylating composition as defined above wherein the base is a compound of formula III or mixtures thereof wherein:
M is selected from potassium and sodium; and
R$^1$ is phenyl optionally substituted with one or more radicals selected from the group consisting of methyl, methyloxy, ethyl, iso-propyl and tert-butyl.

In another embodiment, the invention relates to a process to obtain a trifluoromethylating composition as defined above wherein the amount of base is from 1.1 gram-moles to 4 gram-moles per each gram-atom of copper (I) in the copper (I) source, preferably from 1.2 gram-moles to 2.5 gram-moles per each gram-atom of copper (I) in the copper (I) source, and more preferably is 2 gram-moles per each gram-atom of copper (I) in the copper (I) source.

In another embodiment, the invention relates to a process to obtain a trifluoromethylating composition as defined above wherein the amount of base is from 1.1 gram-moles to 4 gram-moles per each gram-atom of copper (I) in the copper available to form the cuprating reagent, preferably from 1.2 gram-moles to 2.5 gram-moles per each gram-atom of copper (I) in the copper available to form the cuprating reagent, and more preferably is 2 gram-moles per each gram-atom of copper (I) in the copper available to form the cuprating reagent.

In another embodiment, the invention relates to a process to obtain a trifluoromethylating composition as defined above wherein the amount of base is from 0.1 gram-moles to 3 gram-moles per each gram-atom of copper (I) in the copper (I) source, preferably from 1 gram-mole to 1.5 gram-moles per each gram-atom of copper (I) in the copper (I) source, and more preferably is 1 gram-mole per each gram-atom of copper (I) in the copper (I) source.

In another embodiment, the invention relates to a process to obtain a trifluoromethylating composition as defined above wherein the amount of base is from 0.1 gram-moles to 3 gram-moles per each gram-atom of copper (I) in the copper available to form the cuprating reagent, preferably from 1 gram-mole to 1.5 gram-moles per each gram-atom of copper (I) in the copper available to form the cuprating reagent, and more preferably is 1 gram-mole per each gram-atom of copper (I) in the copper available to form the cuprating reagent.

In another embodiment, the invention relates to a process to obtain a trifluoromethylating composition as defined above, wherein:
the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2{}_2$)Br, Cu(SR$^2{}_2$)Cl, Cu(SR$^2{}_2$)I, Cu(OSO$_2$R$^2$) and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
the amount of base is from 1.1 gram-moles to 4 gram-moles per each gram-atom of copper (I) in the copper (I) source, preferably from 1.2 gram-moles to 2.5 gram-moles per each gram-atom of copper (I) in the copper (I) source, and more preferably is 2 gram-moles per each gram-atom of copper (I) in the copper (I) source.

In another embodiment, the invention relates to a process to obtain a trifluoromethylating composition as defined above, wherein:
the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2{}_2$)Br, Cu(SR$^2{}_2$)Cl, Cu(SR$^2{}_2$)I, Cu(OSO$_2$R$^2$) and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
the amount of base is from 1.1 gram-moles to 4 gram-moles per each gram-atom of copper (I) in the copper available to form the cuprating reagent, preferably from 1.2 gram-moles to 2.5 gram-moles per each gram-atom of copper (I) in the copper available to form the cuprating reagent, and more preferably is 2 gram-moles per each gram-atom of copper (I) in the copper available to form the cuprating reagent.

In another embodiment, the invention relates to a process to obtain a trifluoromethylating composition as defined above wherein:
the copper (I) source is selected from CuOR$^2$ and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
the amount of base is from 0.1 gram-moles to 3 gram-moles per each gram-atom of copper (I) in the copper (I) source, preferably from 1 gram-moles to 1.5 gram-moles per each gram-atom of copper (I) in the copper (I) source, and more preferably is about 1 gram-moles per each gram-atom of copper (I) in the copper (I) source.

In another embodiment, the invention relates to a process to obtain a trifluoromethylating composition as defined above wherein:
the copper (I) source is selected from CuOR$^2$ and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
the amount of base is from 0.1 gram-moles to 3 gram-moles per each gram-atom of copper (I) in the copper available to form the cuprating reagent, preferably from 1 gram-moles to 1.5 gram-moles per each gram-atom of copper (I) in the copper available to form the cuprating reagent, and more preferably is about 1 gram-moles per each gram-atom of copper (I) in the copper available to form the cuprating reagent.

In another embodiment, the invention relates to a process to obtain a trifluoromethylating composition as defined above which further comprises a ligand.

In another embodiment, the invention relates to a process to obtain a trifluoromethylating composition as defined above wherein the ligand is selected from 1,10-phenanthroline optionally substituted with one or more groups selected from C$_1$-C$_{20}$ alkyl and C$_1$-C$_{20}$ alkoxy, 2,2'-bipyridyl optionally substituted with one or more groups selected from C$_1$-C$_{20}$ alkyl and C$_1$-C$_{20}$ alkoxy, pyridine optionally substituted with one or more groups selected from C$_1$-C$_{20}$ alkyl and C$_1$-C$_{20}$ alkoxy, quinoline optionally substituted with one or more groups selected from C$_1$-C$_{20}$ alkyl and C$_1$-C$_{20}$ alkoxy, N-heterocyclic carbenes and tertiary phosphines.

In another embodiment, the invention relates to a process to obtain a trifluoromethylating composition as defined above wherein the ligand is selected from 1,10-phenanthroline optionally substituted with one or more groups selected from C$_1$-C$_{20}$ alkyl and C$_1$-C$_{20}$ alkoxy.

In another embodiment, the invention relates to a process to obtain a trifluoromethylating composition as defined above wherein the ligand is 1,10-phenanthroline.

In another embodiment, the invention relates to a process to obtain a trifluoromethylating composition as defined above wherein the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2{}_2$)Br, Cu(SR$^2{}_2$)Cl, Cu(SR$^2{}_2$)I, Cu(OSO$_2$R$^2$) and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
the amount of ligand is such that the amount of base is twice the amount of copper available to form the cuprating reagent.

In another embodiment, the invention relates to a process to obtain a trifluoromethylating composition as defined above wherein
the copper (I) source is selected from CuOR$^2$ and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
the amount of ligand is such that the amount of base is the same as the amount of copper available to form the cuprating reagent.

In another embodiment, the invention relates to a process to obtain a trifluoromethylating composition as defined above wherein the amount of fluoroform is from 0.01 to 1000000 gram-moles per each gram-atom of copper (I) in the copper (I) source, preferably from 0.5 to 100 gram-moles per each gram-atom of copper (I) in the copper (I) source, preferably from 0.5 to 10 gram-moles per each gram-atom of copper (I) in the copper (I) source.

In another embodiment, the invention relates to a process to obtain a trifluoromethylating composition as defined above wherein the amount of fluoroform is 1 gram-mole per each gram-atom of copper (I) in the copper (I) source.

In another embodiment, the invention relates to a process to obtain a trifluoromethylating composition as defined above wherein the concentration of the copper (I) source is from 0.01 to 20 mol per liter of solvent, preferably from 0.05 to 4 mol per liter of solvent, and more preferably 0.5 mol per liter of solvent.

In another embodiment, the invention relates to a process to obtain a trifluoromethylating composition as defined above at a temperature from −30° C. to 100° C., preferably from −30° C. to 80° C., more preferably from −10° C. to 50° C., even more preferably from 15° C. to 30° C., and still more preferably at room temperature.

In another embodiment, the invention relates to a process to obtain a trifluoromethylating composition as defined above, wherein (i) further comprises stirring for from 1 minute to 18 days, preferably stirring for from 1 minute to 48 hours, and more preferably stirring for from 0.1 hours to 10 hours.

In another embodiment, the invention relates to a process to obtain a trifluoromethylating composition as defined above, wherein (i) is performed by mixing the copper (I) source, the base and the solvent in any order and stirring for from 1 minute to 10 hours.

In another embodiment, the invention relates to a process to obtain a trifluoromethylating composition as defined above, wherein (i) is performed by mixing the copper (I) source, the base and the solvent in any order and stirring for from 1 minute to 10 hours; the obtained cuprating reagent being further isolated; preferably by recrystallization; and the isolated compound is further contacted in (ii) with fluoroform in the presence of the solvent.

In another embodiment, the invention relates to a process to obtain a trifluoromethylating composition as defined above wherein the process is performed under a pressure from 0.1 to 50 bar, preferably under atmospheric pressure.

In another embodiment, the invention relates to a process to obtain a trifluoromethylating composition as defined above wherein the cuprating reagent obtained in (i) is used in (ii) by contacting it with fluoroform at stirring for from 1 second to 48 hours, preferably for from 1 minute to 4 hours.

In another embodiment, the invention relates to a process to obtain a trifluoromethylating composition as defined above wherein the trifluoromethylating composition obtained in (ii) is treated with an acid, preferably the acid is selected from the group consisting of hydrogen fluoride, hydrogen fluoride pyridine, mixtures of compounds of formula NR$^3$R$^4$R$^5$ with hydrogen fluoride, melamine/HF, poly[4-vinylpyridinium poly(hydrogen fluoride)], mixtures thereof and B(OR$^6$)$_3$; wherein R$^3$, R$^4$, R$^5$ and R$^6$ are C$_1$-C$_{20}$ alkyl.

In another embodiment, the invention relates to a process to obtain a trifluoromethylating composition as defined above wherein the trifluoromethylating composition obtained in (ii) is treated with an acid, preferably the acid is selected from the group consisting of hydrogen fluoride, hydrogen fluoride pyridine, triethylamine trihydrofluoride, melamine/HF, poly[4-vinylpyridinium poly(hydrogen fluoride)], mixtures thereof and B(OR$^6$)$_3$, wherein R$^6$ is C$_1$-C$_{20}$ alkyl; preferably the acid is selected from the group consisting of hydrogen fluoride, hydrogen fluoride pyridine, triethylamine trihydrofluoride, mixtures thereof and B(OR$^6$)$_3$, wherein R$^6$ is C$_1$-C$_{20}$ alkyl.

In another embodiment, the invention relates to a process to obtain a trifluoromethylating composition as defined above wherein the trifluoromethylating composition obtained in (ii) is treated with an acid selected from the group consisting of hydrogen fluoride, hydrogen fluoride pyridine, triethylamine trihydrofluoride, mixtures thereof and B(OCH$_3$)$_3$.

In another embodiment, the invention relates to a process to obtain a trifluoromethylating composition as defined above wherein:
the trifluoromethylating composition obtained in (ii) is treated with an acid, preferably the acid is selected from the group consisting of hydrogen fluoride, hydrogen fluoride pyridine, mixtures of compounds of formula NR$^3$R$^4$R$^5$ with hydrogen fluoride, melamine/HF, poly[4-vinylpyridinium poly(hydrogen fluoride)] and mixtures thereof; wherein R$^3$, R$^4$ and R$^5$ are C$_1$-C$_{20}$ alkyl; and
wherein the acid is in the amount of from 0.1 to 5 gram-atom of protons per each gram-atom of copper (I) of the trifluoromethylating composition; preferably the acid is in the amount of from 1 to 2 gram-atom of protons per each gram-atom of copper (I) of the trifluoromethylating composition; and more preferably the acid is in the amount of 1 gram-atom of protons per each gram-atom of copper (I) of the trifluoromethylating composition.

In another embodiment, the invention relates to a process to obtain a trifluoromethylating composition as defined above wherein the trifluoromethylating composition obtained in (ii) is treated with an acid selected from the group consisting of hydrogen fluoride, hydrogen fluoride pyridine, triethylamine trihydrofluoride, melamine/HF, poly[4-vinylpyridinium poly(hydrogen fluoride)] and mixtures thereof; and wherein the acid is in the amount of from 0.1 to 5 gram-atom of protons per each gram-atom of copper (I) of the trifluoromethylating composition; preferably the acid is in the amount of from 1 to 2 gram-atom of protons per each gram-atom of copper (I) of the trifluoromethylating composition; and more preferably the acid is in the amount of 1 gram-atom of protons per each gram-atom of copper (I) of the trifluoromethylating composition.

In another embodiment, the invention relates to a process to obtain a trifluoromethylating composition as defined above wherein the trifluoromethylating composition obtained in (ii) is treated with $B(OR^6)_3$ wherein $R^6$ is $C_1$-$C_{20}$ alkyl; and wherein the acid is in the amount of from 0.1 to 10 gram-atom of boron per each gram-atom of copper (I) of the trifluoromethylating composition; preferably the acid is in the amount of from 1 to 2 gram-atom of boron per each gram-atom of copper (I) of the trifluoromethylating composition; and more preferably the acid is in the amount of 1 gram-atom of borons per each gram-atom of copper (I) of the trifluoromethylating composition.

In another embodiment, the invention relates to a process to obtain a trifluoromethylating composition as defined above wherein the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$, and the acid is in the amount of 1 gram-atom of protons or 1 gram-atom of borons per each gram-atom of copper (I) of the trifluoromethylating composition.

In another embodiment, the invention relates to a process to obtain a trifluoromethylating composition as defined above wherein:
the concentration of the copper (I) source is from 0.01 to 20 mol per liter of solvent, preferably from 0.05 to 4 mol per liter of solvent, and more preferably 0.5 mol per liter of solvent; and
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$.

In another embodiment, the invention relates to a process to obtain a trifluoromethylating composition as defined above wherein:
the concentration of the copper (I) source is from 0.01 to 20 mol per liter of solvent, preferably from 0.05 to 4 mol per liter of solvent, and more preferably 0.5 mol per liter of solvent; and
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$, and the acid is in the amount of 1 gram-atom of protons or 1 gram-atom of borons per each gram-atom of copper (I) of the trifluoromethylating composition.

In another embodiment, the invention relates to a process to obtain a trifluoromethylating composition, as defined above wherein the trifluoromethylating composition obtained in (ii) is treated with an acid as defined above; and wherein the acid is added neat.

In another embodiment, the invention relates to a process to obtain a trifluoromethylating composition as defined above wherein the trifluoromethylating composition obtained in (ii) is treated with an acid as defined above; and wherein the acid is added in solution; preferably the solvent is selected from the group consisting of N,N-dimethylformamide (DMF), 1,3-dimethyl-2-imidazolidinone (DMI), N,N-dimethylacetamide (DMAC), 1,3-dimethyl-3,4,5,6-tetrahydro-2(1H)-pyrimidinone (DMPU), N-methylpyrrolidone (NMP), dimethylsulfoxide (DMSO), tetramethylurea (TMU), hexamethylphosphoramide (HMPA) and mixtures thereof; more preferably the acid is added in solution of the solvent used in (i).

In another embodiment, the invention relates to a process to obtain a trifluoromethylating composition as defined above wherein the trifluoromethylating composition obtained in (ii) is treated with an acid preferably the acid is selected from hydrogen fluoride, hydrogen fluoride pyridine, triethylamine trihydrofluoride, melamine/HF, poly[4-vinylpyridinium poly(hydrogen fluoride)] mixtures thereof and compounds of formula $B(OR^6)_3$, wherein $R^6$ is $C_1$-$C_{20}$ alkyl; and wherein the alcohol produced is removed from the mixture under vacuum, via adsorption or via chemisorption.

In another embodiment, the present invention relates to a process to obtain a trifluoromethylating composition as defined above wherein (i), (ii) and the use of the trifluoromethylating composition in the transfer of a trifluoromethyl group to an electrophile are performed by mixing together the solvent, the copper (I) source, the base, fluoroform, the electrophile, and optionally the ligand.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof; and
the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br; [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2_2$)Br, Cu(SR$^2_2$)Cl, Cu(SR$^2_2$)I, Cu(OSO$_2$R$^2$) and mixtures thereof, wherein R$^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy.

In another embodiment, the invention relates to a process to obtain a trifluoromethylating composition as defined above, wherein:
the base is selected from potassium tert-butoxide, sodium, tert-butoxide, potassium methoxide, sodium methoxide and mixtures thereof; and
the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2_2$)Br, $Cu(SR^2{}_2)Cl$, $Cu(SR^2{}_2)I$, $Cu(OSO_2R^2)$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source.

In another embodiment, the invention relates to a process to obtain a trifluoromethylating composition as defined above, wherein:

the base is selected from potassium tert-butoxide, sodium tert-butoxide, potassium methoxide, sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, $Cu(OCOR^2)$, $Cu(SR^2)$, $Cu(SR^2{}_2)Br$, $Cu(SR^2{}_2)Cl$, $Cu(SR^2{}_2)I$, $Cu(OSO_2R^2)$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source; and the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof.

In another embodiment, the invention relates to a process to obtain a trifluoromethylating composition as defined above, wherein:

the base is selected from potassium tert-butoxide, sodium tert-butoxide, potassium methoxide; sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, $Cu(OCOR^2)$, $Cu(SR^2)$, $Cu(SR^2{}_2)Br$, $Cu(SR^2{}_2)Cl$, $Cu(SR^2{}_2)I$, $Cu(OSO_2R^2)$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source; and the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof; and the concentration of the copper (I) source is from 0.01 to 20 mol per liter of solvent, preferably from 0.05 to 4 mol per liter of solvent, and more preferably 0.5 mol per liter of solvent.

In another embodiment, the invention relates to a process to obtain a trifluoromethylating composition as defined above, wherein:

the base is selected from potassium tert-butoxide, sodium tert-butoxide, potassium methoxide, sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, $Cu(OCOR^2)$, $Cu(SR^2)$, $Cu(SR^2{}_2)Br$, $Cu(SR^2{}_2)Cl$, $Cu(SR^2{}_2)I$, $Cu(OSO_2R^2)$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source; and the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof; and the concentration of the copper (I) source is from 0.01 to 20 mol per liter of solvent, preferably from 0.05 to 4 mol per liter of solvent, and more preferably 0.5 mol per liter of solvent; and at a temperature from −30° C. to 100° C., preferably from −30° C. to 80° C., more preferably from −10° C. to 50° C., even more preferably from 15° C. to 30° C., and still more preferably at room temperature.

In another embodiment, the invention relates, to a process to obtain a trifluoromethylating composition as defined above, wherein:

the base is selected from potassium tert-butoxide, sodium tert-butoxide, potassium methoxide, sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, $Cu(OCOR^2)$, $Cu(SR^2)$, $Cu(SR^2{}_2)Br$, $Cu(SR^2{}_2)Cl$, $Cu(SR^2{}_2)I$, $Cu(OSO_2R^2)$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source; and the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof; and the concentration of the copper (I) source is from 0.01 to 20 mol per liter of solvent, preferably from 0.05 to 4 mol per liter of solvent, and more preferably 0.5 mol per liter of solvent; and at a temperature from −30° C. to 100° C., preferably from −30° C. to 80° C., more preferably from −10° C. to 50° C., even more preferably from 15° C. to 30° C., and still more preferably at room temperature; and under a pressure from 0.1 to 50 bar, preferably under atmospheric pressure.

In another embodiment, the invention relates to a process to obtain a trifluoromethylating composition as defined above, wherein:

the base is selected from potassium tert-butoxide, sodium tert-butoxide, potassium methoxide, sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2_2$)Br, Cu(SR$^2_2$)Cl, Cu(SR$^2_2$)I, Cu(OSO$_2$R$^2$) and mixtures thereof, wherein R$^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source; and the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof; and the concentration of the copper (I) source is from 0.01 to 20 mol per liter of solvent, preferably from 0.05 to 4 mol per liter of solvent, and more preferably 0.5 mol per liter of solvent; and at a temperature from −30° C. to 100° C., preferably from −30° C. to 80° C., more preferably from −10° C. to 50° C., even more preferably from 15° C. to 30° C., and still more preferably at room temperature; and under a pressure from 0.1 to 50 bar, preferably under atmospheric pressure; and the trifluoromethylating composition obtained in (ii) is treated with an acid selected from the group consisting of hydrogen fluoride, hydrogen fluoride pyridine, triethylamine trihydrofluoride, mixtures thereof and B(OCH$_3$)$_3$.

In another embodiment, the invention relates to a process to obtain a trifluoromethylating composition as defined above, wherein:

the base is selected from potassium tert-butoxide, sodium tert-butoxide, potassium methoxide, sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2_2$)Br, Cu(SR$^2_2$)Cl, Cu(SR$^2_2$)I, Cu(OSO$_2$R$^2$) and mixtures thereof, wherein R$^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and the amount of base is 2 gram-moles per each gram-atom of copper (I) in the copper (I) source; and the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof; and the concentration of the copper (I) source is from 0.01 to 20 mol per liter of solvent, preferably from 0.05 to 4 mol per liter of solvent, and more preferably 0.5 mol per liter of solvent; and at a temperature from −30° C. to 100° C., preferably from −30° C. to 80° C., more preferably from −10° C. to 50° C., even more preferably from 15° C. to 30° C., and still more preferably at room temperature; and under a pressure from 0.1 to 50 bar, preferably under atmospheric pressure;

the trifluoromethylating composition obtained in (ii) is treated with an acid selected from the group consisting of hydrogen fluoride, hydrogen fluoride pyridine, triethylamine trihydrofluoride, mixtures thereof and B(OCH$_3$)$_3$; and the acid is in the amount of 1 gram-atom of protons or 1 gram-atom of borons per each gram-atom of copper (I) of the trifluoromethylating composition.

In another embodiment, the invention relates to a process to obtain a trifluoromethylating composition as defined above, wherein:

the base is selected from potassium tert-butoxide, sodium tert-butoxide, potassium methoxide, sodium methoxide and mixtures thereof; and the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI(1,10-phenanthroline)]$_2$, copper (I) trifluoroacetate, Cu(OCOR$^2$), Cu(SR$^2$), Cu(SR$^2_2$)Br, Cu(SR$^2_2$)Cl, Cu(SR$^2_2$)I, Cu(OSO$_2$R$^2$) and mixtures thereof, wherein R$^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 2 gram-moles per each gram-atom of copper (I) in the copper (I) source; and
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, $[CuBr(1,10\text{-phenanthroline})]_2$, $[CuCl(1,10\text{-phenanthroline})]_2$, $[CuI(1,10\text{-phenanthroline})]_2$, copper (I) trifluoroacetate, $Cu(OCOR^2)$, $Cu(SR^2)$, $Cu(SR^2_2)Br$, $Cu(SR^2_2)Cl$, $Cu(SR^2_2)I$, $Cu(OSO_2R^2)$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and
the amount of base is 2 gram-moles per each gram-atom of copper (I) in the copper (I) source;
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$; and
the acid is in the amount of 1 gram-atom of protons or 1 gram-atom of borons per each gram-atom of copper (I) of the trifluoromethylating composition.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof; and
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy; and
the amount of base is 1 gram-moles per each gram-atom of copper (I) in the copper (I) source.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source; and
the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2(1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source;
the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2(1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof; and
the concentration of the copper (I) source is from 0.01 to 20 mol per liter of solvent, preferably from 0.05 to 4 mol per liter of solvent, and more preferably 0.5 mol per liter of solvent.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;

the amount of base is 1 gram-moles per each gram-atom of copper (I) in the copper (I) source;
the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof;
the concentration of the copper (I) source is from 0.01 to 20 mol per liter of solvent, preferably from 0.05 to 4 mol per liter of solvent, and more preferably 0.5 mol per liter of solvent; and
at a temperature from −30° C. to 100° C., preferably from −30° C. to 80° C., more preferably from −10° C. to 50° C., even more preferably from 15° C. to 30° C., and still more preferably at room temperature.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source;
the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU); hexamethylphosphoramide (HMPA) and mixtures thereof, preferably the solvent is selected from N,N-dimethylformamide (DMF), N-methylpyrrolidone (NMP) and mixtures thereof;
the concentration of the copper (I) source is from 0.01 to 20 mol per liter of solvent, preferably from 0.05 to 4 mol per liter of solvent, and more preferably 0.5 mol per liter of solvent;
at a temperature from −30° C. to 100° C., preferably from −30° C. to 80° C., more preferably from −10° C. to 50° C., even more preferably from 15° C. to 30° C., and still more preferably at room temperature; and
under a pressure from 0.1 to 50 bar, preferably under atmospheric pressure.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source;
the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoramide (HMPA) and mixtures thereof, preferably the solvent is selected from N,N-dimethylformamide (DMF), N-methylpyrrolidone (NMP) and mixtures thereof;
the concentration of the copper (I) source is from 0.01 to 20 mol per liter of solvent, preferably from 0.05 to 4 mol per liter of solvent, and more preferably 0.5 mol per liter of solvent;
at a temperature from −30° C. to 100° C., preferably from −30° C. to 80° C., more preferably from −10° C. to 50° C., even more preferably from 15° C. to 30° C., and still more preferably at room temperature;
under a pressure from 0.1 to 50 bar, preferably under atmospheric pressure; and
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source;
the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2 (1H)-pyrimidinone (DMPU), N-methylpyrrolidone (NMP), dimethylsulfoxide (DMSO), tetramethylurea (TMU), hexamethylphosphoremide (HMPA) and mixtures thereof, preferably the solvent is selected from N,N-dimethylformamide (DMF), N-methylpyrrolidone (NMP) and mixtures thereof;
the concentration of the copper (I) source is from 0.01 to 20 mol per liter of solvent, preferably from 0.05 to 4 mol per liter, of solvent, and more preferably 0.5 mol per liter of solvent;
at a temperature from −30° C. to 100° C., preferably from −30° C. to 80° C., more preferably from −10° C. to 50° C., even more preferably from 15° C. to 30° C., and still more preferably at room temperature;
under a pressure from 0.1 to 50 bar, preferably under atmospheric pressure; the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$; and
the acid is in the amount of 1 gram-atom of protons or 1 gram-atom of borons per each gram-atom of copper (I) of the trifluoromethylating composition.

In another embodiment, the invention relates to a process to obtain a trifluoromethylating composition as defined above, wherein:

the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source; and
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$.

In another embodiment, the invention relates to a process to obtain a trifluoromethylating composition as defined above, wherein:
the base is selected from potassium tert-butoxide, sodium tert-butoxide, potassium methoxide, sodium methoxide and mixtures thereof;
the copper (I) source is selected from $CuOR^2$ and mixtures thereof, wherein $R^2$ is selected from $C_1$-$C_{20}$ alkyl and $C_5$-$C_7$ aryl, wherein $C_1$-$C_{20}$ alkyl is optionally substituted with one or more $C_5$-$C_7$ aryl, $C_1$-$C_{20}$ alkoxy or $C_5$-$C_7$ aryloxy and wherein $C_5$-$C_7$ aryl is optionally substituted with one or more $C_1$-$C_{20}$ alkyl, $C_1$-$C_{20}$ alkoxy, $C_5$-$C_7$ aryl and $C_5$-$C_7$ aryloxy;
the amount of base is 1 gram-moles per each gram-atom of copper (I) in the copper (I) source;
the trifluoromethylating composition obtained in (ii) is treated with an acid selected from the group consisting of hydrogen fluoride, hydrogen fluoride pyridine, triethylamine trihydrofluoride, mixtures thereof and $B(OCH_3)_3$; and
the acid is in the amount of 1 gram-atom of protons or 1 gram-atom of borons per each gram-atom of copper (I) of the trifluoromethylating composition.

In another embodiment, the invention relates to a process to obtain a trifluoromethylating composition as defined above selected from processes described in examples 1 to 20 and 23 to 37.

In another embodiment, the invention relates to the uses of the trifluoromethylating composition defined above as described in examples 3 to 18 and 26 to 38.

In another embodiment, the invention relates to a process to obtain a trifluoromethylating composition as defined above that is performed in a continuous manner.

In another embodiment, the invention relates to a process to obtain a trifluoromethylating composition as defined above wherein the insoluble inorganic by-products formed in the process are removed from the reaction mixture by solid-liquid separation techniques, preferably by filtration.

In another embodiment, the invention relates to a process to obtain a trifluoromethylating composition as defined above that is performed in a continuous manner and wherein the insoluble formed inorganic by-products are removed from the reaction mixture by filtration.

In another embodiment, the invention relates to the use of the trifluoromethylating composition defined above in the transfer of a trifluoromethyl group to the carbon atom of an organoboron compound wherein the organoboron compound is a boronic acid derivative; preferably the use of the trifluoromethylating composition defined above in the transfer of a trifluoromethyl group to the carbon atom of a boronic acid further comprises an oxidant; and more preferably the oxidant is oxygen, and even more preferably the oxidant is air.

In another embodiment, the invention relates to the use of the trifluoromethylating composition defined above in the transfer of a trifluoromethyl group to an electrophile wherein the electrophile is selected from aryl halides, heteroaryl halides, heterocyclyl halides, alkyl halides, alkynyl halides, alkenyl halides, allyl halides, acyl halides, aryl sulfonates, heteroaryl sulfonates, heterocyclyl sulfonates, alkyl sulfonates, alkynyl sulfonates, alkenyl sulfonates, allyl sulfonates, electron-deficient derivatives of Si, Ge, B, P, As, Sb, Bi, S, Se, Te and a metal atom in a metal compound; and more preferably the electrophile is selected from aryl chlorides, aryl bromides, aryl iodides, heteroaryl chlorides, heteroaryl bromides, heteroaryl iodides, acyl chlorides, acyl bromides, alkyl bromides and alkyl iodides.

In another embodiment, the invention relates to the use of the trifluoromethylating composition defined above wherein the electrophile is selected from an electron-deficient derivative of Si, Ge, B, P, As, Sb, Bi, S, Se and Te, and more preferably selected from an electron-deficient derivative of Si and B.

In another embodiment, the invention relates to the use of the trifluoromethylating composition defined above wherein the electrophile is a metal atom in a metal compound.

In another embodiment, the present invention relates to the use of the trifluoromethylating composition defined above in the transfer of a trifluoromethyl group to a metal atom in a metal compound; preferably the metal is selected from Pd, Pt, Ni, Zn, Cd, Co, Fe, Ru, Rh and Ir.

In another embodiment, the invention relates to the use of the trifluoromethylating composition defined above in the transfer of a trifluoromethyl group to an electrophile in the presence of a catalyst wherein:
the electrophile is selected from aryl halides, heteroaryl halides, heterocyclyl halides, alkyl halides, alkynyl halides, alkenyl halides, allyl halides, acyl halides, aryl sulfonates, heteroaryl sulfonates, heterocyclyl sulfonates, alkyl sulfonates, alkynyl sulfonates, alkenyl sulfonates, allyl sulfonates, electron-deficient derivatives of Si, Ge, B, P, As, Sb, Bi, S, Se, Te and a metal atom in a metal compound; and more preferably the electrophile is selected from aryl chlorides, aryl bromides, aryl iodides, heteroaryl chlorides, heteroaryl bromides, heteroaryl iodides, and electron-deficient derivatives of Si and B; and
preferably the catalyst is selected from metal compounds of Pd, Ni, Pt, Co, Fe, Ru, Rh, Ir and Mn.

In another embodiment, the invention relates to the use of the trifluoromethylating composition defined above in the transfer of a trifluoromethyl group to an electrophile, preferably in the presence of a catalyst, wherein:
the electrophile is selected from aryl halides, heteroaryl halides, alkynyl halides, alkenyl halides, aryl sulfonates, heteroaryl sulfonates, alkynyl sulfonates and alkenyl sulfonates; preferably by mixing together the solvent, the copper (I) source, the base, fluoroform, the electrophile, and the catalyst; and
preferably the catalyst is selected from metal compounds of Pd, Ni, Pt, Co, Fe, Ru, Rh, Ir and Mn.

In another embodiment, the present invention relates to the use of the trifluoromethylating composition obtained in (ii) in the preparation of trifluoromethyl copper complexes by contacting the trifluoromethylating composition obtained in (ii) with one or more ligands, preferably the ligand is selected from 1,10 phenanthroline, triphenylphosphine, 1,3-

Bis(2,6-diisopropylphenyl)imidazol-2-ylidene, 1,3-Bis(2,4,6-trimethylphenyl)imidazol-2-ylidene and mixtures thereof.

In another embodiment, the invention relates to a cuprating reagent of formula I as defined above wherein M is selected from sodium, potassium, rubidium and cesium.

In another embodiment, the invention relates to a cuprating reagent of formula I as defined above wherein M is selected from sodium, potassium, rubidium and cesium; and q is an integer from 1 to 10.

In another embodiment, the invention relates to a cuprating reagent of formula I as defined above wherein M is sodium or potassium.

In another embodiment, the invention relates to a cuprating reagent of formula I as defined above wherein m is an integer between 1 and 20.

In another embodiment, the invention relates to a cuprating reagent of formula I as defined above wherein l is an integer between 1 and 8.

In another embodiment, the invention relates to a cuprating reagent of formula I as defined above wherein m is an integer between 0 and 8.

In another embodiment, the invention relates to a cuprating reagent of formula I as defined above wherein n is an integer between 1 and 8.

In another embodiment, the invention relates to a cuprating reagent of formula I as defined above wherein p is an integer between 2 and 12.

In another embodiment, the invention relates to a cuprating reagent of formula I as defined above wherein q is an integer between 0 and 2.

In another embodiment, the invention relates to a cuprating reagent of formula I as defined above wherein p is twice the value of n.

In another embodiment, the invention relates to a cuprating reagent of formula I as defined above wherein:
l is an integer of between 1 and 8; and
m is an integer of between 0 and 8; and
n is an integer of between 1 and 8; and
p is twice the value of n; and
q is an integer of between 0 and 2.

In another embodiment, the invention relates to a cuprating reagent of formula I as defined above wherein $R^1$ is $C_1$-$C_{20}$ alkyl optionally substituted with one or more $C_5$-$C_7$ aryl, $C_1$-$C_{20}$ alkoxy or $C_5$-$C_7$ aryloxy.

In another embodiment, the invention relates to a cuprating reagent of formula I as defined above wherein $R^1$ is $C_5$-$C_7$ aryl optionally substituted with one or more radicals selected from the group consisting of $C_1$-$C_{20}$ alkyl and $C_1$-$C_{20}$ alkoxy.

In another embodiment, the invention relates to a cuprating reagent of formula I as defined above wherein $R^1$ is phenyl optionally substituted with one or more radicals selected from the group consisting of $C_1$-$C_{20}$ alkyl and $C_1$-$C_{20}$ alkoxy.

In another embodiment, the invention relates to a cuprating reagent of formula I as defined above wherein $R^1$ is phenyl optionally substituted with one or more radicals selected from the group consisting of methyl, methyloxy, ethyl, iso-propyl and tert-butyl.

In another embodiment, the invention relates to a cuprating reagent of formula I as defined above wherein $R^1$ is $C_1$-$C_{20}$ alkyl.

In another embodiment, the invention relates to a cuprating reagent of formula I as defined above wherein $R^1$ is methyl, isopropyl, tert-butyl, iso-butyl, butyl or neo-pentyl; preferably $R^1$ is methyl or tert-butyl; and more preferably $R^1$ is tert-butyl.

In another embodiment, the invention relates to a cuprating reagent of formula I as defined above wherein S is N,N-dimethylformamide.

In another embodiment, the invention relates to a cuprating reagent of formula I as defined above wherein:
X is iodide; and
q is 0 or 2.

In another embodiment, the invention relates to a cuprating reagent of formula I as defined above wherein q is 0.

In another embodiment, the invention relates to a cuprating reagent of formula I as defined above wherein:
X is iodide; and
q is 2.

In another embodiment, the invention relates to a cuprating reagent of formula I as defined above wherein:
M is sodium or potassium; and
$R^1$ is methyl or tert-butyl, preferably $R^1$ is tert-butyl.

In another embodiment, the invention relates to a cuprating reagent of formula I as defined above wherein:
M is sodium or potassium; and
S is N,N-dimethylformamide (DMF).

In another embodiment, the invention relates to a cuprating reagent of formula I as defined above wherein:
$R^1$ is methyl or tert-butyl; and
S is N,N-dimethylformamide (DMF).

In another embodiment, the invention relates to a cuprating reagent of formula I as defined above wherein:
$R^1$ is selected from methyl and tert-butyl;
M is selected from sodium and potassium; and
S is N,N-dimethylformamide (DMF).

In another embodiment, the invention relates to a cuprating reagent of formula I as defined above wherein:
$R^1$ is methyl or tert-butyl;
X is iodide; and
q is 0 or 2.

In another embodiment, the invention relates to a cuprating reagent of formula I as defined above wherein:
S is N,N-dimethylformamide (DMF);
X is iodide; and
q is 0 or 2.

In another embodiment, the invention relates to a cuprating reagent of formula I as defined above wherein:
M is sodium or potassium;
X is iodide; and
q is 0 or 2.

In another embodiment, the invention relates to a cuprating reagent of formula I as defined above wherein:
M is sodium or potassium;
S is N,N-dimethylformamide (DMF);
X is iodide; and
q is 0 or 2.

In another embodiment, the invention relates to a cuprating reagent of formula I as defined above wherein:
M is sodium or potassium; and
p is twice the value of n.

In another embodiment, the invention relates to a cuprating reagent of formula I as defined above wherein:
$R^1$ is methyl or tert-butyl;
S is N,N-dimethylformamide (DMF);
X is iodide; and
q is 0 or 2.

In another embodiment, the invention relates to a cuprating reagent of formula I as defined above wherein:
M is sodium or potassium;
$R^1$ is methyl or tert-butyl;
X is iodide; and
q is 0 or 2.

In another embodiment, the invention relates to a cuprating reagent of formula I as defined above wherein:
M is sodium or potassium;
$R^1$ is methyl or tert-butyl;
S is N,N-dimethylformamide (DMF);
X is iodide; and
q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
X is iodide; and
q is 0 or 2.

In another embodiment, the invention relates to a cuprating reagent of formula I as defined above wherein
l is an integer of between 1 and 8;
m is an integer of between 0 and 8;
n is an integer of between 1 and 8;
p is twice the value of n; and
q is 0.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
X is iodide; and
q is 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
q is an integer of between 0 and 2;
M is sodium or potassium; and
$R^1$ is methyl or tert-butyl, preferably $R^1$ is tert-butyl.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
q is an integer of between 0 and 2;
M is sodium or potassium; and
S is N,N-dimethylformamide (DMF).

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
q is an integer of between 0 and 2;
$R^1$ is methyl or tert-butyl; and
S is N,N-dimethylformamide (DMF).

In another embodiment, the invention relates to a cuprating reagent of formula I as defined above wherein
l is an integer of between 1 and 8;
m is an integer of between 0 and 8;
n is an integer of between 1 and 8;
p is twice the value of n;
q is an integer of between 0 and 2;
$R^1$ is selected from methyl and tert-butyl;
M is selected from sodium and potassium; and
S is N,N-dimethylformamide (DMF).

In another embodiment, the invention relates to a cuprating reagent of formula I as defined above wherein:
l is an integer of between 1 and 8;
m is an integer of between 0 and 8;
n is an integer of between 1 and 8;
p is twice the value of n; and
$R^1$ is methyl or tert-butyl;
X is iodide;
and q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
S is N,N-dimethylformamide (DMF);
X is iodide; and
q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
M is sodium or potassium;
X is iodide; and
q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
M is sodium or potassium;
S is N,N-dimethylformamide (DMF);
X is iodide; and
q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
$R^1$ is methyl or tert-butyl;
S is N,N-dimethylformamide (DMF);
X is iodide; and
q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
M is sodium or potassium;
$R^1$ is methyl or tert-butyl;
X is iodide; and
q is 0 or 2.

In another embodiment, the invention relates to a cuprating reagent of formula I as defined above wherein:
l is an integer of between 1 and 8;
m is an integer of between 0 and 8;
n is an integer of between 1 and 8;
p is twice the value of n;
M is sodium or potassium;
$R^1$ is methyl or tert-butyl;

S is N,N-dimethylformamide (DMF);
X is iodide; and
q is 0 or 2.

In another embodiment, the invention relates to a cuprating reagent of formula [K$_8$Cu$_6$(tert-BuO)$_{12}$(DMF)$_8$I]I.

In another embodiment, the invention relates to a cuprating reagent of formula I selected from the list:
K(DMF)[Cu(tert-BuO)$_2$]; and
Na(DMF)$_2$[Cu(tert-BuO)$_2$].

In another embodiment, the invention relates to a cuprating reagent of formula I selected from the list:
K(DMF)[Cu(tert-BuO)$_2$];
Na(DMF)$_2$[Cu(tert-BuO)$_2$];
[K$_8$Cu$_6$(tert-BuO)$_{12}$(DMF)$_8$(I)]$^+$I$^-$; and
polymers or oligomers thereof.

In some of the processes described along the present invention it may be necessary or advisable to protect the reactive or labile groups by conventional protecting groups. Both the nature of these protecting groups and the procedures for their introduction or removal are well known in the art (see for example Wuts P. G. M y Greene T. W., "Greene's Protective Groups in Organic Synthesis", John Wiley & Sons, 4$^{th}$ edition, 2006). Whenever a protecting group is present, a later deprotection step will be required, which can be performed under standard conditions in organic synthesis, such as those described in the above-mentioned reference.

Unless otherwise stated, in the methods described below the meanings of the different substituents are the meanings described above.

As it will be obvious to those skilled in the art, interconversion reactions can be carried out upon the compounds of the invention as well as upon any suitable synthesis intermediates thereof.

Throughout the description and claims the word "comprises" and variations of the word, are not intended to exclude other technical features, additives, components or steps. Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

In accordance with this invention, it has been discovered that reagents comprising a copper (I) alkoxide adduct in an organic solvent are useful for reacting with fluoroform to directly produce synthetically useful trifluoromethyl copper reagents. The reagents of this invention possess the desirable properties of reactivity toward fluoroform to replace the hydrogen atom on the molecule of HCF$_3$ with the copper atom (cupration), thus giving rise to organocopper compounds having the CuCF$_3$ moiety. These trifluoromethyl copper compounds are useful in a variety of trifluoromethylation reaction to make valuable products.

As disclosed herein, copper (I) sources react with alkali metal alkoxides to produce reagents that can effectively cuprate fluoroform thus producing valuable trifluoromethyl copper compounds. The key is the presence of 2 equivalents of an alkali metal alkoxide per each gram-atom of Cu(I) that can coordinate with the alkoxide base. Contacting such Cu(I) with only one equivalent of alkoxide does not produce the trifluoromethylating composition. In fact, treatment of CuCl with LiOC(CH$_3$)$_3$ in a 1:1 molar ratio is known to produce CuOC(CH$_3$)$_3$ (which may exist as a tetramer), a strong base that can cuprate weak acids (Tsuda, T. et al. Journal of the American Chemical Society 1972, 94, 958 and Lemmen; T. H. et al. Inorganic Chemistry 1990, 29, 3680, incorporated herein by reference). However, when a solution of CuOC(CH$_3$)$_3$ in tetrahydrofuran was prepared as described in these publications, no or little reaction was observed upon contact of this reagent with HCF$_3$ at room temperature (eq 1). Similarly, when this complex was prepared from NaOC(CH$_3$)$_3$ (0.001 gram-mole) or KOC(CH$_3$)$_3$ (0.001 gram-mole) and CuCl (0.001 gram-mole) in N,N-dimethylformamide or N-methylpyrrolidone, adding fluoroform to these reagents resulted in no observable reaction. In contrast, when in these experiments performed in N,N-dimethylformamide or N-methylpyrrolidone, the amount of the alkali metal alkoxide was doubled, efficient cuprating reagents were obtained that easily and cleanly reacted with fluoroform at 25° C. to produce a species containing the CF$_3$Cu moiety in 90-95% yield (eq 2), as determined by $^{19}$F NMR (a singlet at ca. −23 ppm).

The reactive alkoxycuprates that form on treatment of CuX (X=Cl, Br, I) with 2 equiv of MOC(CH$_3$)$_3$ (M=K, Na) were isolated and identified by NMR and single-crystal X-ray diffraction as K(DMF)[Cu(OC(CH3)3)2], Na(DMF)2[Cu(OC(CH3)3)2], and [K8Cu6(OC(CH3)3)12(DMF)8(I)]+I−. These pre-isolated alkoxycuprates were shown to efficiently cuprate fluoroform. Therefore, the cupration process may be run with the alkoxycuprates prepared in situ, that is without isolation or, optionally, as pre-isolated reagents.

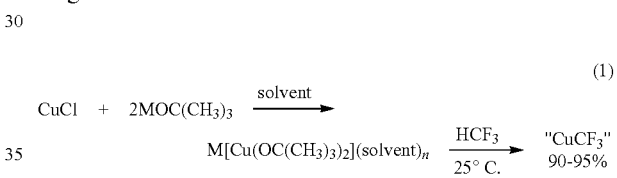

M=K, Na; solvent: N,N-dimethylformamide, N-methylpyrrolidone

The cupration reaction (eq 1) is remarkably selective, exhibiting no sign of fluorine-containing side products, nor intermediate formation of the trifluoromethyl anion that, if formed at room temperature, instantly decomposes to difluorocarbene. The latter is also unstable, dimerizing and undergoing other transformations that lead to products that are observable by $^{19}$F NMR. No such products were observed. Moreover, the trifluoromethyl anion is known to form, under certain conditions, an observable by $^{19}$F NMR hemiaminolate [CF$_3$C(H)N(CH$_3$)$_2$(O)]$^-$ (see, for example: Langlois and Billard, ACS Symposium Series 2005, 911, 57, incorporated herein by reference), which was never observed in these experiments. Performing the cupration in the presence of 2 equiv of styrene or α-methylstyrene did not produce gem-difluorocyclopropanes ($^{19}$F NMR), indicating that the reaction is not mediated by CF$_3^-$ or CF$_2$. Furthermore, when these experiments were repeated in fully deuterated N,N-dimethylformamide, no formation of DCF$_3$ was observed, again indicating that the process did not involve the formation of the trifluoromethyl anion that is formed when fluoroform is simply deprotonated with a strong base. When the KOC(CH$_3$)$_3$ to CuCl ratio was increased to 3:1, the formation of CuCF$_3$ also occurred in nearly quantitative yield. In this experiment, however, side products were detected ($^{19}$F NMR), apparently from the generation of CF$_3^-$/CF$_2$ upon slower deprotonation of CF$_3$H with the extra equivalent of tert-butoxide. In fully deuterated N,N-dimethylformamide, the reaction produced DCF$_3$ among other side products, confirming intermediacy of the trifluoromethyl anion. Carrying out the cupration with a 1.5:1 ratio of t-BuOK to CuCl in DMF gave CuCF$_3$ in only ca. 20% yield. Therefore, the optimal stoichiometry of CuCl and t-BuOK for the generation of an efficient cuprating reagent is 1:2. Therefore, in order to (1) achieve the highest yield of the desired CuCF$_3$ compound and (2) avoid decomposition and wasting of fluoroform, it is critical that the cuprating reagent is produced using two gram-moles of alkoxide per each gram-atom of copper (I) available for coordination with the said alkoxide. It is important to explain what is meant by "copper (I) available for coordination". In certain copper (I) compounds all coordination sites at the metal center are occupied by strongly binding ligands and hence such compounds cannot coordinate to alkoxide and thus form a cuprating reagent. For example, [(1,10-phenanthroline)$_2$Cu]Cl is one such copper(I) compound. This property of strongly binding ligands can be used to render an inactive Cu(I) composition a successful cuprating reagent. This is illustrated by the fact that while a 1:1 mixture of CuCl and MOC(CH$_3$)$_3$ in N,N-dimethylformamide or N-methylpyrrolidone does not react with fluoroform (scheme 1), addition of 1 gram-mole of 1,10-phenanthroline per each 1 gram-mole of CuCl to this mixture produces an active cuprating reagent which produces CuCF$_3$ upon addition of fluoroform. This is because 1,10-phenanthroline, being a strongly binding ligand, sequesters one-half of all copper (I) in the system to form a stable, unreactive complex, thus changing the molar ratio of the alkoxide to "copper (I) available for coordination" to 2:1, which results in the formation of the active cuprating reagent. This is illustrated in Scheme 1.

The yield of the CuCF$_3$ product in this case is approximately 50% because only one-half of the total amount of copper (I) is available for coordination with the alkoxide. The copper (I) source, preferably CuCl, CuBr, or CuI, is contacted with a metal alkoxide and (optionally) a ligand in a solvent to produce the reagent for cupration of fluoroform. The contact is carried out with all reactants dissolved, slurried, or otherwise contained in the liquid phase.

The solvent is an anhydrous aprotic solvent because water and protic solvents hydrolyze, solvolyze and otherwise decompose the metal alkoxide and the cuprating reagent. However, small quantities of water in the system can be tolerated. Thus, running the reaction in DMF containing deliberately added water in the amounts (v/v) 0.005%, 0.01%, 0.05%, 0.1%, and 0.5% produced CuCF$_3$ in 93%, 91%, 97%, and 79%, and 59% yield, respectively. The cuprating reagent and the trifluoromethylating composition are oxygen-sensitive and therefore should be prepared and handled in an inert atmosphere of, for example, nitrogen or argon. Aprotic solvents suitable for the reaction include, but are not limited to, DMF (N,N-dimethylformamide), NMP (N-methylpyrrolidone), DMI (1,3-Dimethyl-2-imidazolidinone), DMPU (1,3-dimethyl-3,4,5,6-tetrahydro-2(1H)-pyrimidinone), DMAC (N,N-dimethylacetamide), TMU (tetramethylurea), HMPA (hexamethylphosphoramide), and mixtures thereof.

The preparation of the cuprating reagent is direct and involves contacting the copper (I) source, the metal alkoxide and (optionally) the ligand in the solvent, preferably at agitation and can take from a few minutes to several hours at room temperature. If the ligand is used, it can be first reacted with the copper salt, followed by addition of the metal alkoxide, or all three compounds are mixed together in the solvent at once. Alternatively, the copper salt can be first reacted with the alkoxide, followed by addition of the ligand. The formation of the cuprating reagent can be performed at any pressure but preferably at about atmospheric.

The cuprating reagent is stable at room temperature and can be used to cuprate fluoroform. To obtain the trifluoromethyl copper compound from the reagent and fluoroform, the two are contacted. Fluoroform is a gas (b. p.=ca. −82° C.) that is easily soluble in organic solvents. Fluoroform can be bubbled through the reagent solution or introduced in the headspace. Fluoroform can be added as a solution in an organic solvent that does not decompose the reagent. Alternatively, the cuprating reagent solution can be added to fluoroform either as a gas or dissolved in an organic solvent. The cupration is most conveniently carried out at room temperature and atmospheric pressure, although lower and higher temperatures and pressures from 0.1 to 50 atm maybe applied if necessary. Depending on conditions used, the cupration process can go to completion after as little as a few seconds to several hours. The cupration reaction can be conveniently monitored by $^{19}$F NMR spectroscopy because Cu—CF$_3$ compounds display signals in the characteristic range of −20 to −40 ppm.

In certain cases, the formation of the cuprating reagent (i) and the cupration (ii) can be performed simultaneously, that is by contacting the copper (I) source, the alkoxide and fluoroform in a solvent in one step. This, however, may result in lower yields because the formation of the cuprating reagent from the copper (I) source and the alkoxide may compete with direct deprotonation of fluoroform to give the trifluoromethyl anion and difluorocarbene which quickly decompose.

Scheme 1

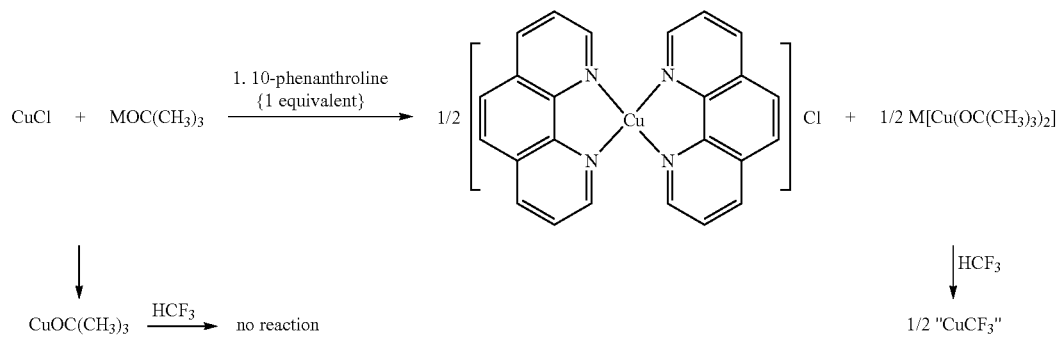

The produced trifluoromethyl copper reagents undergo decomposition at room temperature, unless stabilized as described below. Stability of the $CF_3Cu$ solutions generated from $CF_3H$ and $CuCl$—$KOC(CH_3)_3$ (1:2) in DMF with [Cu]=0.5M at room temperature was studied by measuring $^{19}F$ NMR spectra of the freshly prepared reaction solutions containing $PhCF_3$ as an internal standard (see Examples). The yield of the $CF_3Cu$, as determined 5-10 min after its formation (95%), dropped to approximately 80%, 75%, and 65% after 2, 4, and 18 h, respectively. After that, no significant further decomposition was observed. Similar results were obtained in NMP: the originally measured 96% yield of the $CF_3Cu$ product dropped to 76% after 4 h and further to 68% after 14 h, at which point the decomposition ceased.

At lower concentrations the yields of $CuCF_3$ are higher and the trifluoromethylating reagents are more stable. For instance, at [Cu]=0.75M and 1.0M the measured yields were lower (ca. 70-85%) than at 0.5M concentration of Cu(I) (>90% yield). The decomposition process was accompanied by precipitation of KF (identified by powder X-ray diffraction), which ceased when the decomposition stopped. The following copper complexes were isolated from the partially decomposed solutions and structurally characterized by single-crystal X-ray diffraction: $[Cu(C(OBu-t)_2)(\mu-Cl)]_2$, $[Cu(C(OBu-t)_2)(\mu-Br)]_2$, $[Cu(C(OBu-t)_2)(p-OBu-t)]_2$, and $[Cu(CF_3)Cu(C(OBu-t)_2)(\mu^3-OBu-t)]_2$. These are all bis(tert-butoxy)carbene Cu(I) species indicating that the decomposition of $CuCF_3$ is governed by the formation of a Cu(I) difluorocarbene species that undergo facile nucleophilic displacement of the fluorines with tert-butoxide. The alkali metal cation present in the solution apparently plays a crucial role in the decomposition process by binding to the fluoride to form thermodynamically stable MF.

The spontaneous $CuCF_3$ decomposition can be minimized or suppressed altogether by treatment of the freshly prepared $CuCF_3$ solution with an acid HX that would react with the formally present "one extra equivalent" of $KOC(CH_3)_3$ to give $HOC(CH_3)_3$ and KX. Thus, the resulting trifluoromethylating composition can be further stabilized by an acid HX which aims at sequestering the free alkali cations that are prompt to react with the trifluoromethylating composition to form decomposition products.

The best stabilizers include, but are not limited to, hydrogen fluoride (HF) and its derivatives $Et_3N.3HF$ (TREAT HF), Py.nHF (70% HF), and HF complexes with melamine, polyvinylpyridine, and other bases. Thus, addition of TREAT HF in the amount of ⅓ mol per 1 mol of Cu after the cupration step resulted in precipitation of KF and produced stable solutions of the $CuCF_3$ reagent. Upon treatment with $Et_3N.3HF$, the $^{19}F$ NMR signal from the $CuCF_3$ resonance shifted slightly upfield to −26.3 ppm from its original value of −24.2 ppm, and a new minor singlet resonance appeared in the $CuCF_3$ region at −30.4 ppm, which is assigned to $[Cu(CF_3)_2]^-$. In the $^{13}C$ NMR spectrum of a solution similarly prepared and stabilized with TREAT HF in DMF-$d_7$, the $CF_3$ ligand on Cu of the main $CuCF_3$ species resonated as a quartet at 150.7 ppm ($J_{C-F}$=350 Hz).

Typically, TREAT HF was added within 5-15 minutes after the cupration. Precipitation of KF began instantaneously. Quantitative $^{19}F$ NMR analysis of the resultant solution showed that the total yield of the trifluoromethylcopper species produced was 95%. This yield was calculated on the basis of the $Cu$—$CF_3$ bonds formed, with 85% contribution from a mono-$CF_3$-ligated Cu species (−26.3 ppm) and 10% from $[Cu(CF_3)_2]^-$ (−30.4 ppm). The molar percentage of the $[Cu(CF_3)_2]^-$ was, however, 5% because the Cu atom in this anion bears two $CF_3$ groups. On storage of the solution at room temperature, a minor drop in the original yield of 95% to 93% and 91% was detected after 24 h and 3 days, respectively. An aliquot of the same solution that was stored at −35° C. for 8 days showed no sign of decomposition. The stabilizer may be used in excess. For instance, stabilization with 20% excess of TREAT HF produced similar results.

Furthermore, during the formation of the cuprating reagent from copper chloride and potassium alkoxides, potassium chloride precipitates from the reaction mixture. Similarly, during the stabilization of the trifluoromethylating composition with hydrogen fluoride, either pure or added as derivatives, potassium fluoride precipitates from the reaction mixture. Thus, the inorganic by-products can advantageously be removed from the reaction mixture by solid-liquid separation techniques such as centrifugation and filtration.

The produced trifluoromethyl copper reagents can be used to introduce the trifluoromethyl group into organic and inorganic compounds in manners that are similar to those already known for trifluoromethyl copper reagents obtained by means other than the direct cupration of fluoroform. Both non-stabilized and stabilized solutions can be used, although higher yields are obtained with the stabilized $CuCF_3$ reagents. Thus, the $CuCF_3$ reagents of this invention can be used to prepare trifluoromethylaromatic compounds, as illustrated in Examples below. For instance, the addition of iodobenzene to the $CuCF_3$ compound obtained directly from fluoroform produces trifluoromethylbenzene. The trifluoromethyl reagent prepared by direct cupration of fluoroform may be used in situ for many reactions to introduce the $CF_3$ group into an aromatic ring, into a heteroaromatic ring, into an olefin at a vinylic position, into acetylenic or allylic compounds, into an acyl and aroyl derivatives, as well as for production of trifluoromethyl derivatives of other metals and elements. In certain cases the final trifluoromethylation step may be conveniently combined with the previous step, which is the formation of the trifluoromethyl reagent from fluoroform. In certain other cases, trifluoromethylation reactions with the trifluoromethyl copper reagents made by this invention can be beneficially conducted in the presence of a metal catalyst such as a palladium compound. Examples of such catalytic trifluoromethylation reactions using trifluoromethyl copper reagents prepared by other methods are known: Roche and Dolbier, Journal of Organic Chemistry 1999, 64, 9137; 2000, 65, 5282 (incorporated herein by reference), Liu et al. European Journal of Organic Chemistry 2005, 3680 (incorporated herein by reference) and Journal of Organic Chemistry 2007, 72, 2732 (incorporated herein by reference).

The present invention is beneficial in that it allows for the preparation of valuable trifluoromethyl copper reagents in high yield, directly, selectively and efficiently from fluoroform. Fluoroform is the most attractive trifluoromethyl source, being readily available in large industrial quantities, inexpensive, environmentally benign (not an ozone depleter) and non-toxic. The use of fluoroform as described above is highly economical because the process employs relatively inexpensive chemicals and materials and can be conveniently conducted at room temperature and atmospheric pressure. In contrast, the known indirect processes to produce similar trifluoromethyl copper reagents from fluoroform are multi-step, lower-yielding and less economical because they require use of low temperatures (from −40° C. to −10° C.).

EXAMPLES

The following abbreviations have been used in the examples:
NMR: Nuclear Magnetic Resonance
GC-MS: Gas chromatography coupled with mass spectrometry
DMF: N,N-dimethylformamide
NMP: N-methylpyrrolidone
DMI: 1,3-dimethyl-2-imidazolidinone
DMPU: 1,3-dimethyl-3,4,5,6-tetrahydro-2(1H)-pyrimidinone
DMSO: Dimethylsulfoxide
DMAC: N,N-dimethylacetamide
TMU: Tetramethylurea
HMPA: Hexamethylphosphoramide
THF: Tetrahydrofuran
TREAT•HF: Triethylamine trihydrofluoride
Py•nHF: Hydrogen fluoride pyridine All chemicals were purchased from Aldrich (CuCl, CuBr, MeONa, MeOK, EtOK, EtONa, tert-BuONa, TREAT HF, Py•nHF (70% HF)), Alfa Aesar (CuI, tert-BuOK), and Apollo Scientific ($CF_3H$). All manipulations were performed under argon, unless noted otherwise. Anhydrous DMF, NMP, DMI, DMPU, DMAC, and TMU were used without additional purification. Benzene, toluene, hexanes, ether, and THF were distilled from $Na/OCPh_2$. All solvents, internal standards for quantitative $^{19}F$ NMR analysis, and liquid organic halide reagents were stored over activated 4 Å molecular sieves in a glove-box. $^1H$, $^{13}C$, and $^{19}F$ NMR spectra were recorded on Bruker Avance 400 Ultrashield and Bruker Avance 500 Ultrashield NMR spectrometers. Quantitative $^{19}F$ NMR analyses were carried out with D1=5 s. Single-crystal diffraction studies were carried out using a Bruker-Nonius diffractometer equipped with an APEX III 4K CCD area detector. X-ray powder diffraction analysis was performed on a Bruker D8 Advance powder diffractometer using a transmission configuration. An Agilent Technologies 7890A chromatograph equipped with a 5975C MSD unit was used for GC-MS analysis.

Example 1

Under argon, a 10-mL flask was charged with CuCl (20 mg; 0.2 mmol), potassium tert-butoxide (47 mg; 0.42 mmol), 4,4'-difluorobiphenyl (19 mg; 0.1 mmol; internal standard) and anhydrous, $O_2$-free DMF (1 mL). After the mixture was vigorously stirred for 2 h 30 min at 25° C., a 0.6 mL aliquot of the mixture was placed in a 5-mm NMR tube and capped with a rubber septum under argon. Trifluoromethane (ca. 10 mL) was bubbled through the aliquot in the NMR tube via a syringe needle at room temperature. The solution remained colorless throughout the experiment. Quantitative analysis of the sample by $^{19}F$ NMR indicated that a Cu—$CF_3$ complex (−23.4 ppm) was formed in 90% yield as calculated on the CuCl used.

Example 2

The experiment described in Example 1 above was repeated with NMP as the solvent to produce a Cu—$CF_3$ complex (−23.3 ppm) in 90% yield as calculated on the CuCl used.

Example 3

Under argon, a 10-mL flask was charged with CuCl (100 mg; 1.0 mmol), anhydrous 1,10-phenanthroline (180 mg; 1.0 mmol), potassium tert-butoxide (235 mg; 2.1 mmol), 4,4'-difluorobiphenyl (19 mg; 0.1 mmol; internal standard) and anhydrous, $O_2$-free DMF (2 mL). After the mixture was vigorously stirred for 2 h 30 min at 25° C., a 0.6 mL aliquot of the mixture was placed in a 5-mm NMR tube and capped with a rubber septum under argon. The amount of Cu in the aliquot was therefore 0.3 mmol. Trifluoromethane (ca. 15 mL) was bubbled through this aliquot via a syringe needle at room temperature. Analysis of the sample by $^{19}F$ NMR indicated that a Cu—$CF_3$ complex (−23.4 ppm) was formed in quantitative yield as calculated on the Cu in the sample. Iodobenzene (0.033 mL; 0.3 mmol) was added to the tube via a syringe needle. The formation of small quantities of $PhCF_3$ by $^{19}F$ NMR (−62.2 ppm) was observed after 1 hour. After the tube had been heated at 50° C. for 15 hours, the yield of $PhCF_3$ was 60% (on Cu) at full conversion of the Cu—$CF_3$ complex.

Example 4

Under argon, a 10-mL flask was charged with CuCl (50 mg; 0.5 mmol), anhydrous 1,10-phenanthroline (90 mg; 0.5 mmol), potassium tert-butoxide (117 mg; 1.05 mmol), 1,8-Diazabicyclo[5.4.0]undec-7-ene (DBU; 0.074 mL; 0.5 mmol), 4,4'-difluorobiphenyl (19 mg; 0.1 mmol; internal standard) and anhydrous, $O_2$-free DMF (1.5 mL). After the mixture was vigorously stirred for 2 h 30 min at 25° C., a 0.5 mL aliquot of the mixture was placed in a 5-mm NMR tube and capped with a rubber septum under argon. The amount of Cu in the aliquot was therefore 0.17 mmol. Trifluoromethane (ca. 10 mL) was bubbled through this aliquot in the NMR tube via a syringe needle at room temperature. Analysis of the sample by $^{19}F$ NMR indicated that a Cu—$CF_3$ complex (−23.4 ppm) was formed in 85% yield as calculated on the amount of Cu in the sample. Iodobenzene (0.018 mL; 0.17 mmol) was added to the tube via a syringe needle. After the tube had been heated at 50° C. for 17 hours, the yield of $PhCF_3$ ($^{19}F$ NMR: −62.2 ppm) was 85% (on Cu) at full conversion of the Cu—$CF_3$ complex.

Example 5

Under argon, a 10-mL flask was charged with CuCl (103 mg, 1.04 mmol), anhydrous 1,10-phenanthroline (183 mg, 1.04 mmol), potassium tert-butoxide (160 mg, 1.42 mmol), KF (60 mg, 1.04 mmol) and anhydrous, $O_2$-free DMF (4 mL). After the mixture was vigorously stirred for 1 h 5 min at 25° C., trifluoromethane (45 mL) was slowly added via a glass syringe. After the gas was absorbed in 1.5 h, the mixture was stirred for 40 min, followed by addition of iodobenzene (0.2 mL, 1.88 mmol) and stirring at 25° C. for 19 h, then at 50° C. for 24 h and, finally, at 80° C. for 2 h. The mixture was allowed to cool to room temperature. Analysis of the liquid phase by $^{19}F$ NMR with fluorobenzene as an internal standard (−113.8 ppm) indicated that benzotrifluoride, $PhCF_3$ (−62.1 ppm) was formed in 57% yield (calculated on CuCl used). The formation of benzotrifluoride was confirmed by GC-MS analysis.

Example 6

Under argon, a 10-mL flask was charged with CuCl (33 mg; 0.33 mmol), anhydrous 1,10-phenanthroline (60 mg; 0.33 mmol), potassium tert-butoxide (39 mg; 0.35 mmol), KF (12 mg; 0.2 mmol) and anhydrous, $O_2$-free DMF (2 mL). After the mixture was vigorously stirred for 1 h at 25° C., 4,4'-difluorobiphenyl (16.5 mg; 0.09 mmol) was added as an internal standard. A 0.6 mL aliquot of the resultant solution was placed in a standard 5-mm glass NMR tube. The tube was sealed with a rubber septum and trifluoromethane (20 mL; 0.89 mmol) was slowly bubbled through the solution via a syringe needle. After the addition of $CHF_3$ was complete, iodobenzene (0.1 mL; 0.90 mmol) was added and the tube was placed in the probe of an NMR spectrometer for monitoring at 25° C. The first $^{19}F$ NMR spectrum indicated the formation of a $CF_3$—Cu complex (−24.2 ppm) and trace amounts of $PhCF_3$ (−62.2 ppm). $^{19}F$ NMR spectra were acquired every hour for 60 h to show that the $CuCF_3$ species was converted to $PhCF_3$: the signal at −24.2 ppm was disappearing as the peak at −62.2 ppm grew in intensity. This conversion exceeded 90% and 99% after 24 h and 48 h, respectively. The yield of $PhCF_3$ was 50% (calculated on CuCl used).

Example 7

Under argon, a 10-mL flask was charged with CuCl (106 mg, 1.07 mmol), anhydrous 1,10-phenanthroline (190 mg, 1.07 mmol), sodium methoxide (70 mg, 1.29 mmol) and anhydrous, $O_2$-free DMF (5 mL). After the mixture was vigorously stirred for 1 h at 25° C., trifluoromethane (25 mL) was slowly added via a glass syringe. Approximately 17 mL of the gas were quickly absorbed at stirring. After 1 h iodobenzene (0.15 mL, 1.35 mmol) was added and the mixture was stirred at 25° C. for 18 h, then at 65° C. for 21.5 h and finally at 90° C. for 2 h. The mixture was allowed to cool to room temperature. Analysis of the liquid phase by $^{19}F$ NMR with fluorobenzene as an internal standard (−113.8 ppm) indicated that benzotrifluoride, $PhCF_3$ (−62.1 ppm) was formed in ca. 7% yield (calculated on CuCl used).

Example 8

Under argon, a 10-mL flask was charged with CuCl (105 mg, 1.07 mmol), anhydrous pyridine (1 mL, 12.4 mmol), potassium tert-butoxide (122 mg, 1.08 mmol), KF (12 mg, 0.21 mmol) and anhydrous, $O_2$-free DMF (2 mL). After the mixture was vigorously stirred for 1 h at 25° C., trifluoromethane was slowly added via a glass syringe until gas consumption stopped. The solution was stirred under $CHF_3$ overnight, after which iodobenzene (0.15 mL, 1.41 mmol) was added. The mixture was stirred at 25° C. for 4 h and then at 90° C. for 5 h. Analysis of the liquid phase by $^{19}F$ NMR indicated that benzotrifluoride was formed (−62.1 ppm).

Example 9

Under argon, a 10-mL flask was charged with CuCl (100 mg, 1.04 mmol), potassium tert-butoxide (123 mg, 1.09 mmol) and anhydrous, $O_2$-free DMF (2 mL). After the mixture was vigorously stirred for 45 min at 25° C., tri-n-butylphosphine (0.26 g, 1.29 mmol) and DMF (3 mL) were added. Trifluoromethane was introduced, followed by iodobenzene (0.15 mL, 1.41 mmol). The mixture was stirred for 12 h, after which it was sampled for $^{19}F$ NMR analysis that indicated the formation of a $CuCF_3$ complex (−24 ppm, broad) and no benzotrifluoride. The mixture was then stirred at 80° C. for 24 h. Analysis of the liquid phase by $^{19}F$ NMR indicated that benzotrifluoride was formed (−62.1 ppm).

Example 10

Under argon, a 10-mL flask was charged with CuCl (100 mg, 1.04 mmol), potassium tert-butoxide (120 mg, 1.08 mmol) and anhydrous, $O_2$-free DMF (3 mL). After the mixture was vigorously stirred for 7 h at 25° C., KF (60 mg, 1.04 mmol) and DMF (1 mL) were added. The mixture was stirred under trifluoromethane for 19 h, after which as solution of 4-nitroiodobenzene (0.28 g, 1.12 mmol) in anhydrous DMF (1 mL) and anhydrous pyridine (1 mL) was added. The mixture was stirred at 80° C. for 3 h. Analysis of the liquid phase by $^{19}F$ NMR indicated that 4-nitrobenzotrifluoride was formed (−62.5 ppm).

Example 11

Under argon, a 10-mL flask was charged with CuCl (100 mg, 1.04 mmol), pyridine (1 mL) and DMF (1 mL). The mixture was stirred until most of the solids had dissolved to produce a slightly cloudy solution. To this solution was added potassium methoxide (100 mg, 1.43 mmol), trifluoromethane was introduced and the mixture was stirred for 5 h at 25° C. and then 10 min at 70° C. Iodobenzene (0.15 mL, 1.41 mmol) was then added and the mixture was stirred for 12 h at 25° C. and then 70-80° C. for 8 h. Analysis of the liquid phase by $^{19}F$ NMR indicated that $PhCF_3$ was formed (−62.2 ppm).

Example 12

Under argon, a 10-mL flask was charged with CuCl (92 mg, 0.93 mmol), potassium tert-butoxide (122 mg, 1.08 mmol) and anhydrous, $O_2$-free DMSO (3 mL). After the mixture was vigorously stirred for 15 min at 25° C., iodobenzene (0.11 mL, 1.03 mmol) was added. The mixture was stirred under trifluoromethane for 2 h at 25° C., 1 h at 65° C. and then 16 h at 80° C. Analysis of the mixture by $^{19}F$ NMR indicated that $PhCF_3$ was produced (−60.5 ppm).

Example 13

Under argon, a 10-mL flask was charged with CuCl (91 mg, 0.93 mmol), potassium tert-butoxide (122 mg, 1.08 mmol) and anhydrous, $O_2$-free DMF (4 mL). After the mixture was vigorously stirred for 3.5 h at 25° C., iodobenzene (0.11 mL, 1.03 mmol) was added. The mixture was stirred under trifluoromethane for 18.5 h at 25° C., 1 h at 65° C. and then 3 h at 80° C. Analysis of the mixture by $^{19}F$ NMR indicated the formation of a $CuCF_3$ complex (−25.5 ppm) and $PhCF_3$ (−62.0 ppm).

Example 14

Under argon, a 10-mL flask was charged with CuCl (90 mg, 0.92 mmol), anhydrous 1,10-phenanthroline (180 mg, 1 mmol), potassium tert-butoxide (120 mg, 1.08 mmol), KF (60 mg, 1.04 mmol) and anhydrous, $O_2$-free DMF (5 mL). After the mixture was vigorously stirred for 1 h at 25° C., trifluoromethane (28 mL) was slowly added via a glass syringe. After the gas was absorbed, at stirring, in ca. 30 min, iodobenzene (0.15 mL, 1.41 mmol) was added and stirring at 25° C. continued for 20 h. Then the mixture was stirred for 15 h at 65° C. and for 2 h at 90° C. for 2 h. The mixture was allowed to cool to room temperature. Analysis of the liquid phase by $^{19}F$ NMR with fluorobenzene as an internal standard (−113.8 ppm) indicated that benzotrifluoride, $PhCF_3$ (−62.0 ppm) was formed in 43% yield (calculated on CuCl used). The formation of benzotrifluoride was confirmed by GC-MS analysis.

Example 15

Under argon, a 10-mL flask was charged with CuI (20 mg, 0.1 mmol), anhydrous 1,10-phenanthroline (19 mg, 0.1 mmol), KF (60 mg, 1.04 mmol), iodobenzene (0.11 mL, 1.03 mmol) and anhydrous, $O_2$-free DMF (1 mL). To this mixture, under $CHF_3$, was slowly (1 h) added at stirring a solution of potassium tert-butoxide (160 mg, 1.42 mmol) in DMF (2 mL). After the mixture was stirred overnight at 25° C. the temperature was raised to 80° C. and the reaction continued for 13 h. Analysis of the liquid phase by $^{19}F$ NMR with fluorobenzene as an internal standard (−113.8 ppm) indicated that benzotrifluoride, $PhCF_3$ (−62.1 ppm) was formed in 40% yield (calculated on CuI used).

Example 16

A 180-mL Fischer-Porter tube was charged, under argon, with CuCl (107 mg, 1.08 mmol), 1,10-phenanthroline monohydrate (220 mg, 1.11 mmol), KF (260 mg, 4.5 mmol), anhydrous, $O_2$-free DMF (1 mL), THF (2 mL), potassium tert-butoxide (0.80 g, 7.1 mmol) and iodobenzene (0.4 mL, 3.66 mmol). The tube was pressurized with trifluoromethane to 2.72 atm and the mixture was stirred first at 25° C. for 24 h and then at 70° C. for 4 h. Analysis of the liquid phase by $^{19}F$ NMR indicated that benzotrifluoride, $PhCF_3$ (−62.1 ppm) was formed.

Example 17

A 15-mL glass pressure tube was charged, under argon, with CuCl (100 mg, 1.01 mmol), 4,4'-Di-t-butyl-2,2'-bipyridyl (270 mg, 1.01 mmol), DMF (1 mL), THF (1 mL), iodobenzene (0.12 mL, 1.13 mmol) and sodium tert-butoxide (150 mg, 1.56 mmol). After the tube was pressurized with $CHF_3$ to 1.36 atm the mixture was stirred at 25° C. for 18 days. Analysis of the liquid phase by GC-MS and $^{19}F$ NMR indicated that $PhCF_3$ was produced.

Example 18

A 180-mL Fischer-Porter tube was charged, under argon, with [1,3-Bis(2,6-diisopropylphenyl)imidazol-2-ylidene] copper chloride (100 mg, 0.2 mmol), iodobenzene (0.45 mL, 4.23 mmol), THF (5 mL) and a freshly ground, under argon, mixture of KF (1.0 g, 17.33 mmol) and KOH (1.0 g, 17.82 mmol). The tube was pressurized with $CHF_3$ to 2.18 atm and stirred at 25° C. for 4 h, 50° C. for 2.5 h, 60° C. for 1 h and then at 80° C. for 28 h. Analysis of the liquid phase by $^{19}F$ NMR indicated that benzotrifluoride, $PhCF_3$ (−62.0 ppm) was produced.

Example 19

(a) A mixture of CuCl (50 mg; 0.51 mmol), tert-BuOK (118 mg; 1.05 mmol), DMF (1 mL), and PhF (50 μL; 0.53 mmol; internal standard) was stirred for 30 min. A 0.6 mL aliquot of the resultant cloudy solution was placed in a 5-mm NMR tube that was then capped with a rubber septum and brought out. Fluoroform gas (15 mL; 0.67 mmol) was bubbled through the solution via a syringe needle. The reaction was complete within seconds. $^{19}F$ NMR analysis of the sample 10-15 min after the reaction indicated that a $CuCF_3$ species (−24.0 ppm) was produced in 90-95% yield. No other $^{19}F$ NMR-detectable products were observed. (b) Similar results were obtained in NMP. (c) Repeating the experiment with CuCl in the presence of styrene (2 equiv) produced identical results; neither gem-difluorophenylcyclopropane nor any other side products were detected. (d) No formation of 1,1-difluoro-2-methyl-2-phenylcyclopropane was observed in a repeat using CuI as the Cu(I) source and α-methylstyrene (2 equiv) as a $CF_2$ trap.

Example 20

Stability Studies

A 3-oz Fischer-Porter tube equipped with a pressure gauge, a needle valve, and a Teflon-coated magnetic stir-bar was charged with CuCl (0.50 g; 5.05 mmol), tert-BuOK (1.19 g; 10.62 mmol), DMF (10 mL), and $PhCF_3$ (123 μL; 1.00 mmol; internal standard). After the mixture was stirred for 30 min at room temperature, the sealed tube was brought out and evacuated on a vacuum line to ca. 1 mm Hg. At vigorous stirring, fluoroform was introduced to ca. 50 psi, after which the pressure dropped to 5-10 psi within a few seconds. $^{19}F$ NMR analysis of the sample 10-15 min after the reaction indicated that a $CuCF_3$ species (−24.2 ppm) was produced in 95% yield. Decomposition of the product was monitored by $^{19}F$ NMR (Table 1; Experiment #1). As the decomposition occurred, the singlet $^{19}F$ NMR signal from $CuCF_3$ was slightly shifting upfield from −24.2 to −25.6 ppm. Note that the cupration reaction may be performed in a standard flask by bubbling $CF_3H$ through the dialkoxycuprate solution. However, the developed procedure in Fischer-Porter tubes provides better protection of the reagents and products from accidental exposure to air. This experiment was repeated to demonstrate reproducibility of the results (Table 1; Experiment #2).

TABLE 1

Spontaneous decomposition of $CuCF_3$ species generated from $CF_3H$ and CuCl– tert-BuOK (1:2) in DMF with [Cu] = 0.5M at 22-25° C.

| Experiment #1 | | Experiment #2 | |
| --- | --- | --- | --- |
| Time, h | $CuCF_3$ yield, % | Time, h | $CuCF_3$ yield, % |
| 0.1 | 95 | 0.1 | 94 |
| 0.7 | 87 | 0.5 | 89 |
| 1.2 | 84 | 1.0 | 85 |
| 1.7 | 80 | 1.5 | 81 |
| 2.5 | 77 | 2.3 | 78 |
| 3.1 | 76 | 2.9 | 76 |
| 4.0 | 74 | 3.4 | 75 |
| 4.2 | 72 | 4.2 | 72 |
| 17.7 | 64 | 17.5 | 65 |
| 23.5 | 64 | 23.4 | 65 |
| 42.5 | 61 | 42.3 | 63 |

Example 21

Synthesis and Isolation of K(DMF)[Cu(tert-BuO)$_2$]

A mixture of CuCl (0.50 g; 5.05 mmol) and tert-BuOK (1.18 g; 10.54 mmol) in DMF (5 mL) was vigorously stirred for 30 min at room temperature. Filtration of the mixture produced solid KCl that was identified by powder X-ray diffraction after washing with ether (5 mL). The ether washing and the filtrate were combined and kept at −35° C. for 20 h. The white needle-shaped crystals were separated by filtration, washed with cold ether (2×0.5 mL), and dried under vacuum. The yield was 1.043 g (64%). The structure of K(DMF)[Cu(tert-BuO)$_2$] was established by single-crystal X-ray diffraction. $^1H$ NMR($C_6D_6$, 25° C.), δ: 7.70 (s, 1H, DMF), 2.41 (s, 3H, DMF), 1.94 (s, 3H, DMF), 1.60 (s, 18H, tert-Bu). $^{13}$C NMR(C$_6$D$_6$, 25° C.), δ: 162.9 (s, CH, DMF), 69.5 (s, C, tert-Bu), 37.3 (s, CH$_3$, tert-Bu), 35.7 (s, CH$_3$, DMF), 31.3 (s, CH$_3$, DMF).

Example 22

Synthesis and Isolation of Na(DMF)$_2$[Cu(tert-BuO)$_2$]

(a) DMF (2 mL) was added, at stirring, to a mixture of CuCl, (51 mg; 0.51 mmol) and tert-BuOK (109 mg; 1.13 mmol). The copper salt quickly dissolved and a large amount of needle-shaped crystals precipitated out within 5-10 seconds to produce a thick suspension. Gently heating the mixture to ca. 50-55° C. resulted in dissolution of the white needles. The cloudy solution was filtered warm to remove insoluble NaCl. The solid-free, colorless filtrate produced uniformly shaped, very thin, air- and moisture sensitive white needle crystals on cooling to room temperature. The structure of the product Na(DMF)$_2$[Cu(tert-BuO)$_2$] was established by single-crystal X-ray diffraction. (b) A mixture of CuCl (253 mg; 2.56 mmol), tert-BuOK (508 mg; 5.29 mmol), and DMF (10 mL) was stirred at 50-55° C. for 30 min and filtered warm. The solid NaCl was washed with ether (5 mL). The ether washing and the filtrate were combined and kept at −35° C. for 1.5 h. The white solid was separated by filtration, with ether (0.5 mL), hexanes (15 mL), and dried under vacuum. The yield was 883 mg (91% if calculated for Na(DMF)$_2$[Cu(tert-BuO)$_2$]). However, $^1$H NMR indicated that the DMF to tert-BuO ratio in the solid was <1. $^1$H NMR (THF-d$_8$, 25° C.), δ: 7.92 (s, 1.5H, DMF), 2.88 (s, 4.5H, DMF), 2.77 (s, 4.5H, DMF), 1.18 (s, 18H, tert-Bu). $^{13}$C NMR(C$_6$D$_6$, 25° C.), δ: 162.6 (s, CH, DMF), 68.8 (s, C, tert-Bu), 36.9 (br s, CH$_3$, tert-Bu), 36.1 (s, CH$_3$, DMF), 31.2 (s, CH$_3$, DMF).

Example 23

Preparation of CuCF$_3$ from Fluoroform in NMP

Stabilization effect. A 3-oz Fischer-Porter tube equipped with a pressure gauge, a needle valve, and a Teflon-coated magnetic stir-bar was charged with CuCl (0.50 g; 5.05 mmol), tert-BuOK (1.20 g; 10.71 mmol), NMP (10 mL), and PhF (187 µL; 2.00 mmol; internal standard). After the mixture was stirred for 30 min at room temperature, the sealed tube was brought out and quickly evacuated on a vacuum line to ca. 1 mm Hg. At vigorous stirring, fluoroform was introduced to ca. 50 psi, after which the pressure dropped to 5-10 psi within a few seconds. $^{19}$F NMR analysis of the sample 10-15 min after the reaction indicated that a CuCF$_3$ species (−24.9 ppm) was produced in 96% yield. Within 5-10 min, a 5-mL aliquot of this solution was withdrawn and treated with TREAT HF (135.5 µL; 0.83 mmol). Decomposition of CuCF$_3$ in the unstabilized and stabilized solutions was monitored by $^{19}$F NMR. Without the stabilization, the yield of CuCF$_3$ dropped to 76% and 67% after 4 and 14 h, respectively. In contrast, the total yield of CuCF$_3$ (−26.9 ppm) including 3% of [Cu(CF$_3$)$_2$]$^−$ (−31 ppm) in the stabilized solution after 4 and 14 h was 92% and 90%, respectively.

Example 24

Preparation of CuCF$_3$ from Fluoroform in DMF

Stabilization Effect of TREAT HF. A 3-oz Fischer-Porter tube equipped with a pressure gauge, a needle valve, and a Teflon-coated magnetic stir-bar was charged with CuCl (0.50 g; 5.05 mmol), tert-BuOK (1.18 g; 10.54 mmol), DMF (10 mL), and PhF (187 µL; 2.00 mmol; internal standard). After the mixture was stirred for 30 min at room temperature, the sealed tube was brought out and quickly evacuated on a vacuum line to ca. 1 mm Hg. At vigorous stirring, fluoroform was introduced to ca. 50 psi, after which the pressure dropped to 5-10 psi within a few seconds. After 5 min, a solution of TREAT HF (272 µL; 1.67 mmol) in DMF (1 mL) was added. A 1-mL aliquot was withdrawn and placed in a freezer at −35° C. By $^{19}$F NMR, the yield of the stabilized solution stored at room temperature under argon was 94%, 92%, 90%, and 89% (including 5% of [Cu(CF$_3$)$_2$]$^−$, −30.4 ppm) after 0.2, 13, 60, and 80 h, respectively. In the 1-mL sample of the same stabilized solution stored at −35° C. the yield was 93% after 80 h.

Example 25

Stabilization of the CuCF$_3$ Reagent with TREAT HF in Excess

A 3-oz Fischer-Porter tube equipped with a pressure gauge, a needle valve, and a Teflon-coated magnetic stir-bar was charged with CuCl (0.50 g; 5.05 mmol), tert-BuOK (1.18 g; 10.54 mmol), DMF (10 mL), and PhF (187 µL; 2.00 mmol; internal standard). After the mixture was stirred for 30 min at room temperature, the sealed tube was brought out and quickly evacuated on a vacuum line to ca. 1 mm Hg. At vigorous stirring, fluoroform was introduced to ca. 50 psi, after which the pressure dropped to 5-10 psi within a few seconds. After 5 min, a solution of TREAT HF (326 µL; 2.00 mmol) in DMF (1 mL) was added. By $^{19}$F NMR, the yield of the stabilized solution stored at room temperature under argon was 97%, 92%, and 89% (including 3% of [Cu(CF$_3$)$_2$]$^−$, −30.4 ppm) after 0.2, 10, and 38 h, respectively. This experiment shows that use of TREAT HF in 20% excess provides neither extra stabilization, nor destabilization to the CuCF$_3$ reagent.

Example 26

Trifluoromethylation Reactions with Stabilized CuCF$_3$ Reagents Derived from CF$_3$H A 3-oz Fischer-Porter tube equipped with a pressure gauge, a needle valve, and a Teflon-coated magnetic stir-bar was charged with CuCl (0.50 g; 5.05 mmol), tert-BuOK (1.18 g; 10.54 mmol), DMF (10 mL), and PhF (187 µL; 2.00 mmol; internal standard). After the mixture was stirred for 30 min at room temperature, the sealed tube was brought out and quickly evacuated on a vacuum line to ca. 1 mm Hg. At vigorous stirring, fluoroform was introduced to ca. 50 psi, after which the pressure dropped to 5-10 psi within a few seconds. After 15 min, a solution of TREAT HF (272 µL; 1.67 mmol) in DMF (1 mL) was added. By $^{19}$F NMR, the yield of the stabilized solution was 98% (including 3% of [Cu(CF$_3$)$_2$]$^−$; −31 ppm). This solution was used in a series of trifluoromethylation reactions. For each aromatic trifluoromethylation reaction, to 0.6 mL of this solution (0.21 mmol of CuCF$_3$) placed in a 5-mm NMR tube was added an organic halide (0.32 mmol) and the mixture was heated at 50° C. (oil bath). The results of these experiments are summarized in Table 2. In another experiment, 0.1 mL of this solution (0.035 mmol of CuCF$_3$) was added to [(tmeda)Pd(Ph)(I)] (15 mg; 0.035 mmol) in DMF (0.5 mL). After 5.5 h at room temperature, full conversion to [(tmeda)Pd(Ph)

(CF$_3$)] was observed by $^{19}$F NMR (δ=−19.8 ppm). In another experiment, to 0.6 mL of the CuCF$_3$ solution (0.21 mmol) was added CH$_3$I (80 μL, 6-fold excess). After 1.5 days at room temperature, full conversion of the CuCF$_3$ reagent was observed by $^{19}$F NMR. The yield of CF$_3$CH$_3$ (−59.6 ppm, q, $J_{F-H}$=13 Hz) present in the liquid phase was 28%. The total yield could not be determined because of the distribution of the 1,1,1-trifluoroethane product (bp=−47° C.) between the solution and the gas phase.

0.25 mmol) in DMF-d$_7$ (0.3 mL) produced [(IPr)Cu(CF$_3$)] quantitatively. $^1$H NMR (DMF-d$_7$, 25° C.), δ: 7.98 (s, 2H, IPr), 7.60 (t, 2H, J=7.7 Hz, arom CH), 7.48 (d, 4H, J=7.7 Hz, arom CH), 2.64 (m, 4H, J=7.0 Hz, i-Pr CH), 1.32 (d, 12H, J=7.0 Hz, i-Pr CH$_3$), 1.27 (d, 12H, J=7.0 Hz, i-Pr CH$_3$). Signals from tert-BuOH were also observed in the $^1$H NMR spectrum at 4.23 ppm (s, 2H, OH) and at 1.19 ppm (s, 18H, CH$_3$). $^{19}$F NMR (DMF-d$_7$, 25° C.), δ: −30.7 (s, CuCF$_3$).

TABLE 2

Aromatic trifluoromethylation reactions with CF$_3$H-derived CuCF$_3$ reagents at 50° C. (Example 26).

| substrate | reaction time, h | product | $^{19}$F NMR conversion of CuCF$_3$, % | $^{19}$F NMR yield, % |
|---|---|---|---|---|
| Ph-I | 25 | Ph-CF$_3$ | >95 | 80-85 |
| 4-Me-C$_6$H$_4$-I | 25 | 4-Me-C$_6$H$_4$-CF$_3$ | >99 | 75-80 |
| 4-Cl-C$_6$H$_4$-I | 25 | 4-Cl-C$_6$H$_4$-CF$_3$ | >95 | 90-95 |
| 4-MeO-C$_6$H$_4$-I | 25 | 4-MeO-C$_6$H$_4$-CF$_3$ | >99 | 70-75 |
| 4-F-C$_6$H$_4$-I | 25 | 4-F-C$_6$H$_4$-CF$_3$ | >95 | 75 |
| 2-I-pyridine | 16 | 2-CF$_3$-pyridine | >99 | 95-99 |
| 2-Br-pyridine | 16 | 2-CF$_3$-pyridine | >99 | 30 |
| 2-I-thiophene | 25 | 2-CF$_3$-thiophene | >99 | 85-90 |

Example 27

A mixture of CuCl (50 mg; 0.51 mmol), tert-BuOK (118 mg; 1.05 mmol), DMF-d$_7$ (1.3 mL), and PhF (187 μL; 2 mmol; internal standard) was stirred for 30 min. A 0.65 mL aliquot of the resultant cloudy solution was placed in a 5-mm NMR tube that was then capped with a rubber septum and brought out. Fluoroform gas (15 mL; 0.67 mmol) was bubbled through the solution via a syringe needle. $^{19}$F NMR analysis of the sample 10-15 min after the reaction indicated that a CuCF$_3$ species (−23.0 ppm) was formed in >95% yield. Treatment of this solution with IPrH$^+$ Cl$^−$ (105 mg;

Example 28

The experiment described in Example 24 was repeated with DMF as the solvent. The yield of CuCF$_3$ in the stabilized solution was 95%. After iodobenzene (34 μL; 1.5 equiv) was added to a 0.6 mL aliquot of the thus prepared solution and the mixture was heated at 80° C. for 16 h, $^{19}$F NMR analysis indicated full conversion of the CuCF$_3$ reagent and 86% yield of benzotrifluoride. Another 0.6 mL aliquot of the CuCF$_3$ solution was treated with 4-fluoroiodobenzene (35 μL; 1.5 equiv) and then heated at 80° C. for 16 h. $^{19}$F NMR analysis indicated full conversion of the CuCF$_3$ reagent and 76% yield of 4-fluorobenzotrifluoride.

Example 29

The experiment described in Example 28 was repeated with DMI as the solvent. The yield of CuCF$_3$ in the stabilized solution was 97%. After iodobenzene (34 µL; 1.5 equiv) was added to a 0.6 mL aliquot of the thus prepared solution and the mixture was heated at 80° C. for 16 h, $^{19}$F NMR analysis indicated full conversion of the CuCF$_3$ reagent and 86% yield of benzotrifluoride. Another 0.6 mL aliquot of the CuCF$_3$ solution was treated with 4-fluoroiodobenzene (35 µL; 1.5 equiv) and then heated at 80° C. for 16 h. $^{19}$F NMR analysis indicated full conversion of the CuCF$_3$ reagent and 76% yield of 4-fluorobenzotrifluoride.

Example 30

The experiment described in Example 28 was repeated with NMP as the solvent. The yield of CuCF$_3$ in the stabilized solution was 98%. After iodobenzene (34 µL; 1.5 equiv) was added to a 0.6 mL aliquot of the thus prepared solution and the mixture was heated at 80° C. for 16 h, $^{19}$F NMR analysis indicated full conversion of the CuCF$_3$ reagent and 77% yield of benzotrifluoride. Another 0.6 mL aliquot of the CuCF$_3$ solution was treated with 4-fluoroiodobenzene (35 µL; 1.5 equiv) and then heated at 80° C. for 16 h. $^{19}$F NMR analysis indicated full conversion of the CuCF$_3$ reagent and 67% yield of 4-fluorobenzotrifluoride.

Example 31

The experiment described in Example 28 was repeated with TMU as the solvent. The yield of CuCF$_3$ in the stabilized solution was 87%. After iodobenzene (34 µL; 1.5 equiv) was added to a 0.6 mL aliquot of the thus prepared solution and the mixture was heated at 80° C. for 4 h, $^{19}$F NMR analysis indicated full conversion of the CuCF$_3$ reagent and 78% yield of benzotrifluoride. Another 0.6 mL aliquot of the CuCF$_3$ solution was treated with 4-fluoroiodobenzene (35 µL; 1.5 equiv) and then heated at 80° C. for 4 h. $^{19}$F NMR analysis indicated full conversion of the CuCF$_3$ reagent and 79% yield of 4-fluorobenzotrifluoride.

Example 32

The experiment described in Example 28 was repeated with DMAC as the solvent. The yield of CuCF$_3$ in the stabilized solution was 99%. After iodobenzene (34 µL; 1.5 equiv) was added to a 0.6 mL aliquot of the thus prepared solution and the mixture was heated at 80° C. for 4 h, $^{19}$F NMR analysis indicated >99% conversion of the CuCF$_3$ reagent and 88% yield of benzotrifluoride. Another 0.6 mL aliquot of the CuCF$_3$ solution was treated with 4-fluoroiodobenzene (35 µL; 1.5 equiv) and then heated at 80° C. for 4 h. $^{19}$F NMR analysis indicated >99% conversion of the CuCF$_3$ reagent and 84% yield of 4-fluorobenzotrifluoride.

Example 33

Preparation of CuCF$_3$ from Fluoroform in DMF

Stabilization with Py•nHF (70% HF). A 3-oz Fischer-Porter tube equipped with a pressure gauge, a needle valve, and a Teflon-coated magnetic stir-bar was charged with CuCl (0.50 g; 5.05 mmol), tert-BuOK (1.18 g; 10.54 mmol), DMF (10 mL), and PhF (187 µL; 2.00 mmol; internal standard). After the mixture was stirred for 30 min at room temperature, the sealed tube was brought out and quickly evacuated on a vacuum line to ca. 1 mm Hg. At vigorous stirring, fluoroform was introduced to ca. 50 psi, after which the pressure dropped to 5-10 psi within a few seconds. After 5 min, a solution of Py•nHF (70% HF) (131 µL; 1.67 mmol) in DMF (1 mL) was added. By $^{19}$F NMR, the yield of CuCF$_3$ in the thus stabilized solution stored at room temperature under argon was 99% and (including 4% of [Cu(CF$_3$)$_2$]$^-$, −30.4 ppm) and 96% after 0.2 and 17 h, respectively. To a 0.6 mL aliquot of this solution, was added 4-fluoroiodobenzene (15 µL; 0.65 equiv) and the mixture was heated at 100° C. for 30 min. $^{19}$F NMR analysis indicated full conversion of the CuCF$_3$ reagent and 88% conversion of 4-fluoroiodobenzene to 4-fluorobenzotrifluoride.

Example 34

To a 0.31 M solution of stabilized CuCF$_3$ in DMF (2.5 mL; 0.78 mmol) was added a solution of PPh$_3$ (617 mg; 2.35 mmol) in dry DMF (1.5 mL). After stirring overnight the mixture was treated with ether (10 mL). The white precipitate of [(Ph$_3$P)$_3$Cu(CF$_3$)] was separated by filtration, washed with ether (3×5 mL), and dried under vacuum. The yield was 347 mg (48%). NMR (CH$_2$Cl$_2$, 25° C.): $^{31}$P, δ=−0.6 ppm (br, s); $^{19}$F, δ=−25.4 ppm (s). Purity ($^{19}$F with an internal standard): 97%.

Example 35

To a stabilized 0.475 M CuCF$_3$ solution in DMF (2.1 mL; 1.0 mmol) was added phenylboronic acid PhB(OH)$_2$ (61 mg, 0.5 mmol). Air was slowly bubbled through this mixture at agitation at 40° C. (oil bath). When the reaction mixture thickened 15-20 min after the beginning of the reaction, an additional quantity of DMF (0.5 mL) was added. After 4 h, the heating was removed and 1,3-bis(trifluoromethyl)benzene (39 µL; 0.25 mmol) was added as an internal standard. The reaction mixture was diluted with water and extracted with ether. Quantitative $^{19}$F NMR analysis of the organic layer indicated that benzotrifluoride was produced in ca. 100% yield.

Example 36

To a stabilized 0.367 M CuCF$_3$ solution in DMF (0.6 mL; 0.22 mmol) was added α-bromoacetophenone (22 mg; 0.11 mmol) and the solution was heated at 50° C. (oil bath) under argon for 3 h. After allowing the mixture to cool to room temperature, 1,3-bis(trifluoromethyl)benzene (internal standard) was added, the mixture was diluted with water, and extracted with ether. GC-MS and quantitative $^{19}$F NMR analysis of the ether extract indicated that α-(trifluoromethyl)acetophenone was formed in 52% yield. $^{19}$F NMR: −62.6 ppm (t, J=9.7 Hz). MS: 188 (m/z).

Example 37

Under argon, to a vigorously stirred solution of Pd$_2$ dba$_5$ (35 mg; 2.5 mol %), Xanthphos (29 mg; 5 mol %), and 4-t-butylphenyl bromide (0.17 mL; 1 mmol) in DMF (5 mL) heated at 125° C. (oil bath) was slowly added over a period of 2 h (syringe pump) a 0.367 M solution of CuCF$_3$ in DMF (5 mL; 1.84 mmol). After the addition of the CuCF$_3$ solution was finished, the mixture was kept at 125° C. for 10 min and then allowed to cool to room temperature. An internal standard (1,3-bis(trifluoromethyl)benzene) was added and a 0.3-mL sample of the mixture was withdrawn, diluted with water; and extracted with ether. GC-MS and quantitative $^{19}$F NMR analysis of the ether extract indicated that 4-t-butylbenzotrifluoride was produced in 13% yield (corresponds to 2.6 turnovers on the amount of Pd used). $^{19}$F NMR: −62.9 (s). MS: 202 (m/z).

Example 38

To a stabilized 0.385 M CuCF$_3$ solution in DMF (0.6 mL; 0.23 mmol) was added p-toluic acid chloride (20 μL; 0.15 mmol) and the solution was heated at 60° C. (oil bath) under argon for 1.5 h. After allowing the mixture to cool to room temperature, fluorobenzene (internal standard) was added. GC-MS and quantitative $^{19}$F NMR analysis of the mixture indicated that trifluoromethyl p-tolyl ketone was formed in 25% yield. $^{19}$F NMR: −71.7 ppm (s). MS: 188 (m/z).

The invention claimed is:

1. A process to obtain a trifluoromethylating composition which comprises:
   (i) contacting a copper (I) source and a base in the presence of a solvent; and
   (ii) reacting the cuprating reagent obtained in (i) and fluoroform.

2. The process according to claim 1, wherein the base is selected from alkali metal alkoxide, alkali metal aryloxide and mixtures thereof.

3. The process according to claim 1, wherein the solvent is selected from N,N-dimethylformamide (DMF), 1,3-dimethyl-2-imidazolidinone (DMI), N,N-dimethylacetamide (DMAC), 1,3-dimethyl-3,4,5,6-tetrahydro-2(1H)-pyrimidinone (DMPU), N-methylpyrrolidone (NMP), dimethylsulfoxide (DMSO), tetramethylurea (TMU), hexamethylphosphoramide (HMPA) and mixtures thereof.

4. The process according to claim 1, wherein:
   the copper (I) source is selected from copper (I) chloride, copper (I) bromide, copper (I) iodide, copper (I) cyanide, copper (I) oxide, copper (I) trifluoromethanesulfonate, copper (I) thiocyanate, [Cu[1,3-bis(2,6-diisopropylphenyl)imidazol-2-ylidene]Cl, [Cu[1,3-bis(2,6-diisopropylphenyl)imidazol-2-ylidene]Br, [CuBr(1,10-phenanthroline)]$_2$, [CuCl(1,10-phenanthroline)]$_2$, [CuI (1,10-phenanthroline)]$_2$, copper (I) trifluoroacetate, Cu(OCOR$^2$), Cu(SR$^2$), Cu(SR$^2{}_2$)Br, Cu(SR$^2{}_2$)Cl, Cu(SR$^2{}_2$)I, Cu(OSO$_2$R$^2$) and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
   the amount of base is from 1.1 gram-moles to 4 gram-moles per each gram-atom of copper (I) in the copper (I) source.

5. The process according to claim 1, wherein:
   the copper (I) source is selected from CuOR$^2$ and mixtures thereof, wherein R$^2$ is selected from C$_1$-C$_{20}$ alkyl and C$_5$-C$_7$ aryl, wherein C$_1$-C$_{20}$ alkyl is optionally substituted with one or more C$_5$-C$_7$ aryl, C$_1$-C$_{20}$ alkoxy or C$_5$-C$_7$ aryloxy and wherein C$_5$-C$_7$ aryl is optionally substituted with one or more C$_1$-C$_{20}$ alkyl, C$_1$-C$_{20}$ alkoxy, C$_5$-C$_7$ aryl and C$_5$-C$_7$ aryloxy; and
   the amount of base is from 0.1 gram-mole to 3 gram-moles per each gram-atom of copper (I) in the copper (I) source.

6. The process according to claim 1, wherein the copper (I) source is selected from copper (I) chloride, copper (I) bromide, copper iodide and mixtures thereof.

7. The process according to claim 1, wherein the trifluoromethylating composition obtained in (ii) is treated with an acid selected from hydrogen fluoride, hydrogen fluoride pyridine, mixtures of compounds of formula NR$^3$R$^4$R$^5$ with hydrogen fluoride, melamine/HF, poly[4-vinylpyridinium poly(hydrogen fluoride)], mixtures thereof and B(OR$^6$)$_3$; wherein R$^3$, R$^4$, R$^5$ and R$^6$ are C$_1$-C$_{20}$ alkyl.

8. The process according to claim 7, wherein:
   the trifluoromethylating composition obtained in (ii) is treated with an acid selected from the group consisting of hydrogen fluoride, hydrogen fluoride pyridine, triethylamine trihydrofluoride, mixtures thereof and B(OCH$_3$)$_3$; and
   the acid is in the amount of 1 gram-atom of protons or 1 gram-atom of borons per each gram-atom of copper (I) of the trifluoromethylating composition.

9. The process according to claim 1, that is performed in a continuous manner.

10. The process according to claim 1, wherein the base is a compound of formula III or mixtures thereof:

M-OR1      III wherein:
   M is potassium or sodium; and
   R1 is C1-C20 alkyl or C5-C7 aryl, wherein C1-C20 alkyl is optionally substituted with one or more C5-C7 aryl, C1-C20 alkoxy and C5-C7 aryloxy, and wherein C5-C7 aryl is optionally substituted with one or more C1-C20 alkyl, C1-C20 alkoxy, C5-C7 aryl and C5-C7 aryloxy.

11. The process according to claim 10, wherein the base is selected from potassium tert-butoxide, sodium tert-butoxide, potassium methoxide and mixtures thereof.

* * * * *